US006921530B1

(12) United States Patent
Smith

(10) Patent No.: US 6,921,530 B1
(45) Date of Patent: Jul. 26, 2005

(54) LOW DOSE IL-2 FOR POTENTIATION OF IMMUNITY

(75) Inventor: Kendall A. Smith, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 643 days.

(21) Appl. No.: 09/708,635

(22) Filed: Sep. 22, 2000

Related U.S. Application Data

(60) Provisional application No. 60/156,097, filed on Sep. 24, 1999.

(51) Int. Cl.[7] .............................................. A61K 45/00
(52) U.S. Cl. ................... 424/85.2; 424/208.1; 530/351
(58) Field of Search ......................... 424/188.1, 208.1, 424/85.2, 198.1

(56) References Cited

U.S. PATENT DOCUMENTS

| 4,933,433 | A |   | 6/1990 | Tamblyn |
| 4,938,956 | A |   | 7/1990 | Howard |
| 4,940,456 | A |   | 7/1990 | Sibalis |
| 5,126,129 | A |   | 6/1992 | Wiltrout |
| 5,420,109 | A |   | 5/1995 | Suto |
| 6,045,788 | A | * | 4/2000 | Smith ........................ 424/85.2 |
| 6,190,656 | B1 | * | 2/2001 | Lane et al. ................. 424/85.2 |
| 6,509,313 | B1 | * | 1/2003 | Smith ............................ 514/2 |

FOREIGN PATENT DOCUMENTS

| WO | WO 97/31622 | 4/1997 | ........................ 9/6 |
| WO | WO 97/41831 | 11/1997 | |

OTHER PUBLICATIONS

Kakumu, S., et al., 1988, "Pilot study of recombinant human interleukin 2 for chronic type B hepatitis", Hepatol. 8(3):487–492.*

Tilg, H., et al., 1993, "Pilot study of natural human interleukin–2 in patients with chronic hepatitis B: Immunomodulatory and antiviral effects", J. Hepatol. 19:259–267.*

Pardo, M., et al., 1997, "A pilot study of recombinant interleukin–2 for treatment of chronic hepatitis C", Hepatol. 26(5):1318–1321.*

Newman, M. J., and M. F. Powell, 1995, "Immunological and formulation design considerations for subunit vaccines", in Vaccin Design: The Subunit and Adjuvant Approach, Powell, M. F., and M. J. Newman, eds., Plenum Press, New York, pp. 1–42.*

Gursel, M., et al., 1998, "The immunological co–adjuvant action of liposomal interleukin–2: the role of mode of localisation of the cytokine and antigen in the vesicles", J. Drug Target. 5(2):93–98.*

Barouch, D. H., et al., 1998, "Augmentation and suppression of immune responses to an HIV–1 DNA vaccine by plasmid cytokine/lg administration", J. Immunol. 161(4):1875–82.*

Vandamme, A. M., et al., 1998, "Anti–human immunodeficiency virus drug combination strategies", Antivir. Chem. Chemo. 9:187–203.*

Tilg, H., et al., 1993, "Pilot study of natural human interleukin–2 in patients with chronic hepatitis B", J. Hepatol. 19:259–267.*

Tsai, S. L., and S. N. Huang, 1997, "T cell mechanisms in the immunopathogenesis of viral hepatitis B and C", J. Gastroenterol. Hepatol. 12 (Suppl.):S227–S235.*

Caligiuri, Selective Modulation of Human Natural Killer Cells In Vivo After Prolonged Infusion of Low Dose Recombinant Interleukin 2, Journal of Clinical Investigation, 1993, p. 123–132.

Teppler, Efficacy of Low Doses of the Polyethylene Glycol Derivative of Interleukin–2 in Modulating the Immune Response of Patients with Human Immunodeficiency Virus Type 1 Infection, Journal of Infectious Diseases, 1993; 167:291–298.

Anderson, Effects of Route and Formulation on Clinical Pharmacokinetics of Interleukin–2, Clinical Pharmacokinetics, 1994, 27; 1:19–31.

Yamamoto, Hepatic Arterial Infusion of Interleukin–2 in Advanced Hepatocellular Carcinoma, Acta Oncologica, 1993, 32; 1:43–51.

Jacobson, Rational Interleukin 2 Therapy for HIV Positive Individuals: Daily Low Doses Enhance Immune Function Without Toxicity, Proceedings of the National Academy of Sciences of the United States of America, 1996, 93:10405–10410.

Meuer, Low Dose Interleukin–2 Induces Systemic Immune Responses Against HBsAg In Immunodefecient Non–Responders to Hepatitis B Vaccination, The Lancet, 1989, No. 8628, 00. 15–18.

Bernstein, Prolonged Administration of Low–Dose Interleukin–2 in Human Immunodeficiency Virus–Associated Malignancy Results in Selective Expansion of Innate Immune Effectors Without Significant Clinical Toxicity, Blood, 1995, 86; 9:3287–3294.

Lechman, et al., Hepatology, 1996, 24:790–795.

Missale, et al., J.Clin.Invest., 1996, 98:706–714.

Caligiuri, et al., Journal of Clinical Oncology, 1991, 9:2110–2119.

Rehermann, et al., J.Clin.Invest., 1996, 98:1432–1440.

Hiroishi, et al., Hepatology, 1997, 25:705–712.

Koziel, et al., J.Clin.Invest., 1995, 96:2311–2321.

Guidotti, et al., Proc. Natl. Acad. Sci. USA, 1994, 91:3764–3768.

(Continued)

Primary Examiner—Jeffrey S. Parkin
(74) Attorney, Agent, or Firm—Darby & Darby

(57) ABSTRACT

Low doses of IL-2 are administered to potentiate an immune response after antiviral treatment. IL-2 is also administered in conjunction with immunotherapy to enhance the immune response to infection.

8 Claims, 5 Drawing Sheets

OTHER PUBLICATIONS

Tsui, et la., Proc. Natl. Acad. Sci. USA, 1995, 92:12398–12402.

Guidotti, et al., Immunity, 1996, 4:25–36.

Tilg, et al., Journal of Heptalogy, 1993, 10:259–267.

Artillo, et al., Journal of Medical Virology, 1998, 54:167–172.

Pardo, et al., Hepatology, 1997, 26:1318–1321.

Schlaak, et al., Hepatology, AASLD Abstracts, 1998, 28:1380.

Uberti–Foppa, et al., Hepatology, AASLD Abstracts, 1998, 28:1249.

* cited by examiner

LOW DOSE IL-2 FOR POTENTIATION OF IMMUNITY

This application claims benefit of 60/156,097 filed Sep. 24, 1999.

This work was supported by grants from the National Institutes of Health, the National Institute of Allergy and Infections Diseases, Bethesda, Md.

FIELD OF THE INVENTION

This application relates to the field of potentiation of an immune response by administering low dose interleukin-2 prior to vaccination or after antiviral treatment has been discontinued.

BACKGROUND OF THE INVENTION

Immunity to Infectious Agents

It is well known that a number of viruses remain latent after the primary infection has been cleared by the immune system, including Epstein Barr Virus, Herpes Simplex Virus, Varicella-Zoster Virus and Ctyomegalovirus (Boldogh, I. et al., *Medical Microbiology*, 4th edition, Ed. S. Baron, The University of Texas Medical Branch at Galveston, 1996, pp. 585–596). However, should the host become immunocompromised, often the latent infection becomes productive once again. Cell-mediated immunity plays a dominant role in maintaining the latent state of a virus (Janeway, C. and P. Travers, *Immunobiology, The Immune System in Health and Disease*, Garland Publishing Inc., New York, 1997, pp. 9-1 to 9-49). Other viruses, such as human immunodeficiency virus (HIV) and hepatitis viruses (Hepatitis A virus (HAV), hepatitis B virus (HBV), hepatitis C virus (HCV), have a latent phase followed by chronic infection and pathology.

Antigen-specific acquired immunity, mediated by memory T cells of both the T-helper (TH) and cytotoxic T lymphocyte (CTL) classes, is very important for recognizing and reacting to productively-infected cells. Innate host defense mechanisms are promoted by NK cells via the production of cytokines, such as interferon-gamma (IFN-γ), granulocyte-monocyte colony stimulating factor (GM-CSF), and tumor necrosis factor-alpha (TNF-α). These cytokines are potent stimuli for monocytes/macrophages, and they activate phagocytic cells to process and present antigen to T cells and to kill intracellular organisms. Prior to exposure, or as long as the virus remains latent and the viral genome is not transcribed or translated, the immune system cannot recognize the infected cell. However, once the cell begins to express the viral genome it will be recognized by the immune system and killed via natural killer (NK) cells and CTL (Janeway, C. and P. Travers. supra).

Cytokines

Cytokines are small proteins secreted primarily, but not exclusively, by cells of the immune system. These proteins regulate the proliferation and/or differentiative functions of other cells. Examples of cytokines include interleukins, interferons, hematopoietic colony stimulating factors (CSF), and proinflammatory factors such as tumor necrosis factor (TNF). The cytokines are primarily responsible for regulating the immune system. They determine the onset, magnitude, and duration of the immune response by stimulating the proliferation and differentiation of various types of cells comprising the immune system, including all of the white blood cells (leukocytes) that are recognizable as lymphocytes, monocytes/macrophages, polymorphonuclear leukocytes (PMN), and specialized antigen-presenting cells (APCs). However, the high and sometimes intolerable toxicities associated with cytokine administration have precluded their widespread use, especially in asymptomatic individuals afflicted with an infection or illness, such as HIV.

Until recently, the view was widely held that the use of cytokines was ineffective in some diseases, and contraindicated, for example in patients with HIV infection due to its potential for activating or increasing replication of HIV.

Immune Regulation of HIV

Studies of individuals who are long-term HIV positive, but nonprogressors, indicate that the immune system is capable of containing the virus in a latent state, without detectable plasma virus, and with normal circulating CD4+ T cells (Rosenberg, E. S. et al., *Science* 278:5342, 1997). CD4+ T cells capable of proliferating in vitro in response to HIV antigens are detectable in these individuals, and may be important for the containment of the virus in a latent state. CD8+ HIV-specific CTL and NK cells are also thought to be important in containing the virus in a latent, non-replicating form.

Antiviral therapy with pharmaceuticals that inhibit the replication of virus such as HIV have been found to decrease plasma virus to undetectable levels. Combination antiviral HIV therapy with Protease Inhibitors (PI) and Reverse Transcriptase (RT) inhibitors has provided Highly Active Antiviral Therapy (HAART) (Hammer, S. M. et al., *N. Engl. J. Med.* 337:725–733, 1997; Gulick, R. M. et al., *N. Engl. J. Med.* 337:734–739, 1997). HAART results in the rapid cessation of viral replication and the decline of plasma virus to undetectable levels within 4–8 weeks. However, in most instances, HAART alone does not lead to complete immune recovery.

Because the antiviral drugs only inhibit replicating virions, a residual viral load is left as latent provirus integrated within the host genome. Recent studies estimate the pool to be on the order of 1–10 million infected cells, and that many of these cells are long-lived memory T cells that may persist for many years. Thus, when HAART is discontinued, viral replication usually resumes and plasma virus rises to detectable levels within a few weeks. If HAART is then reinstituted, plasma viral levels once again decline, and at the same rate observed initially. Antiviral therapy for as long as two and a half years has not eradicated latent provirus.

Moreover, it now appears that many individuals may not be able to take HAART indefinitely, due to serious long-term side effects. As many as 40%–60% of patients who have received HAART for greater than one year have developed symptoms of Cushing's Syndrome, with hyperglycemia, hyperlipidemia, centipetal fat distribution, and peripheral muscle wasting (P. Yeni, Fourth International AIDS Congress (1998). Accordingly, indefinite HAART is no longer feasible.

Recently, as a supplement to antiviral therapy, low doses of cytokines have been administered to patients in attempts to still retain at least some of the immune enhancing effects, while hoping to circumvent the toxicities associated with cytokine administration.

Low doses of agents having IL-2 activity (e.g., about 100,000 to about 500,000 IU IL-2/m$^2$ body surface of an agent having specific activity of 15×10$^6$ IU/mg protein) have been found to be effective when continuously administered to patients for prolonged periods of time to activate and/or stimulate the immune system in the substantial absence of toxicity. These agents are suitable for the chronic stimulation and/ or maintenance of immune responses in subjects without eliciting substantial toxicity, i.e., WHO Group 1 or higher, when administered at doses effective to activate high affinity IL-2 receptors. This is the subject of co-pending U.S. application Ser. No. 08/608,516; WO97/03306, which is disclosed herein by reference in its entirety.

Individuals with HIV infection treated with daily IL-2 for more than two years in conjunction with HAART exhibited no side effects, had complete reconstitution of circulating low dose lymphocytes, and improved immune function. Daily low-dose IL-2 therapy served to correct the deficiency in CD4+ T cells, while maintaining the high frequency of CD8+ HIV-specific CTL, and increasing the circulating NK cells. An individual who received a year of HAART plus IL-2 therapy exhibited a viral load which had been reduced to very low levels, and a high frequency of HIV-specific TH and CTFLS, as well as a 5 to 10-fold increase in NK cells. Tests for Delayed Type Hypersensitivity (DTH) to common environmental antigens more than doubled after 6 months of IL-2 therapy.

HCV

Hepatitis C virus is a major cause of chronic hepatitis, cirrhosis and hepatic cancer in this country. It is estimated that 1.4% of Americans have been infected with HCV (almost 4 million people), and that 10,000 die each year as a consequence of HCV infection. For comparison, only 500,000 to one million Americans are infected with HIV. Hepatic failure due to chronic HCV infection is the most common indication for liver transplantation. Of those who are infected with HCV, only about 10% clear the virus from their body, and achieve normal liver function by blood tests. These people are said to have "resolved" their infection. Another 25% of infected people have evidence of HCV RNA in their bloodstream but have normal liver function. However, the vast majority (65–70%) of those infected with HCV have measurable HCV in their bloodstream and abnormal liver function tests, yet they remain asymptomatic and unaware of their infection, known as chronic active hepatitis (CAH). A large portion of patients (20%) with CAH proceed to develop cirrhosis, while others go on to develop fulminant liver failure (5–10%) or hepatocellular carcinoma (less than 5%). Other complications of CAH are cryoglobulinemia, glomerulonephritis, and porphyria cutanea tarda (DiBisceglie, A. et al., *Hepatology: A textbook of Liver Disease* 3rd Edition, W B Saunders 1996; Sherlock, *Current Opinion Gstroenerology*, 12: 217–223, 1996; Murphy, E L et al. *Jama* 275(13): 995–1000, 1996).

Both humoral (antibody mediated) and cellular (T cell mediated) immunity to HCV have been described. However, it is believed that resolution of HCV infection requires the activation and recruitment of HCV specific T-lymphocytes, in addition to inhibition of viral replication. Thus, individuals who achieve a sustained virologic response have a readily detectable HCV antigen-specific T cell response, while individuals who fail to respond, or who relapse after cessation of therapy, do not have easily detectable T cell reactivity to HCV. In one study, PMBC proliferation in response to the NS3 protein during acute HCV infection was highly correlated with resolution of infection. A different study showed stronger and more frequent T cell proliferative responses in those individuals with resolved HCV disease compared with those who had chronic disease (Lechmann, M. et al., *Hepatology* 24(4): 790–5, 1996; Missale G., et al., *J. Clin. Invest.* 98(3): 706–14, 1996). The absolute number of CD4+ T cells is highly correlated with HCV viral load (both in HIV negative and HIV+ individuals) (Caligiuri M., et al., *J. Clin. Oncol.* 9: 2110–2119, 1991). In contrast, those with chronic disease are more likely to have mounted only antibody responses against HCV proteins. HLA class I restricted CTLs have also been described against HCV. Their role in the development of protective immunity to HCV is not clear, but several investigators have established that a more vigorous CTL response is correlated with lower HCV viral loads (Rehermann, B., *J. Clin. Invest.* 98(6): 1432–40, 1996; Hiroishi, K., *Hepatology* 25(3): 705–12, 1997; Koziel, M J, et al., *J. Clin. Invest.* 96(5): 2311–21, 1995).

Work on hepatitis B virus (HBV) infections has shown that cytotoxic T lymphocytes are very important in limiting viral production, not necessarily entirely via cytolysis of virus-infected cells, but also via the release of the antiviral cytokines IFN-γ and TNF-α (Guidotti, L G, et al., *Proc. Natl. Acad. Sci.* 91(9): 3764–8, 1994). The mechanism of the cytokine-induced antiviral effect has been attributed to an accelerated diminution of viral RNA transcription (Tsui, L V, et al., *Proc. Natl. Acad. Sci. USA* 92(26): 12398–12402, 1995). Further work has shown that IFN-γ and TNF-α activate two independent viracidal pathways: the first pathway eliminates HBV nucleocapsid particles and their cargo of replicating viral genomes, while the second pathway destabilizes viral RNA (Guidotti, L G, et al., *Immunity* 4(1): 25–36, 1996).

Natural killer cells are an important element in host defense against many viral infections, though their role in response to HCV has not been studied thus far.

Thus, while HCV is not completely eradicated by the immune response in chronically infected patients, it is responsive to CTL-mediated control.

Currently Accepted Therapy of HCV

Until very recently, Inteferon-α (IFN-α) was the only therapy for HCV infection proven to be effective. A cytokine produced by macrophages and lymphocytes, IFN-α is known to have anti-viral effects by inhibiting steps in both viral transcription and translation. At doses of 3×10$^6$ units administered subcutaneously three times a week over the course of one year, IFN-α monotherapy induced a sustained response in 35% of patients (range 28–43%) (Poynard, T., *Hepatology* 24(4): 778–89, 1996).

Although clearly an immunostimulatory cytokine, the relative therapeutic contribution of the immunostimulatory effects of IFN appear to be secondary to its antiviral effects. Notably, even though a high CTLp frequency is associated with a decrease in HCV viral burden, IFN-α therapy does not increase the CTLp frequency, even in those who ultimately clear HCV (Rehermann, B. et al, *J. Clin. Invest.* 98(6): 1432–40, 1996). The combination of IFN-α and ribivarin have proven more effective. After one year of therapy, the IFN-α-ribavarin combination yielded a 38% sustained response as measured by disappearance of plasma virus (McHutchison, J G, et al. *N. Engl. J. Med.* 339(21): 1485–92, 1998). Despite these successes, additional therapeutic intervention is needed for the majority of individuals who become infected.

Interferon-α

IFN-α has antiviral, immunomodulatory, and antiproliferative effects. Produced by monocytes and lymphocytes, it upregulates MHC class I on many cell types. IFN-α also potentiates the cytolytic capacity of both CD8+ T cells and NK cells (reviewed in Durum, S. et al., *Fundamental Immunology 3rd Edition*: Raven Press, 1993), and promotes the differentiation of macrophages by increasing their phagocytic, antigen processing and presentation capacities and their microbicidal activity.

Although there are several mechanisms which induce production of IFN-α, one of the most important is the presence of double stranded RNA (dsRNA), exclusively a viral product. In the presence of dsRNA, IFN-α activates enzymes which degrade mRNA, both of viral and host origin, which results in the inhibition of protein synthesis, thus inhibiting viral replication (Biron, C A, *Semin Immunol.* 10(5): 383–90, 1998). One study on HCV dynamics after IFN-α therapy showed a biphasic decline in plasma HCV viral load during daily IFN therapy (Newmann, A U, et al., *Science* 282(5386): 103–7, 1998). After an initial delay of 9 hours, viral load decreased very rapidly, by between $10^3$ and $10^5$ copies per ml per day for the first 24 hours to 48 hours. Thereafter, the rate of viral decline slowed to between 5 and 25% of initial decline depending on the dose of IFN. Although the antiviral mechanism of IFN action in HCV is not known, this pattern of viral decline is most compatible with blocking viral production and release by infected cells, rather than preventing the infection of new cells.

By inhibiting overall cellular protein synthesis, IFN-α also has marked antiproliferative effects on target cells. The antiproliferative effects have been exploited in the therapy of some malignancies, but these effects are not limited to malignancies, so that the dose limiting toxicity of IFN-α is usually myelosuppression.

Therapy with IFN-α has been approved by the FDA for the following diseases: Hairy cell leukemia, Condyloma accuminata, AIDS related Kaposi's Sarcoma, HBV, and HCV. The dose of IFN-α varies by disease from 3 million units (15 μg) three times a week for hepatitis C, to 50 million units (250 μg) daily for multiple myeloma.

Ribavirin

Ribavirin is a synthetic nucleoside analog with antiviral activity in vitro against a variety of RNA and DNA viruses. In monotherapy of HCV it has been shown to be of some benefit in biochemical response, though not virologic response. Several recent studies have shown a synergistic effect with IFN-α in HCV, although by unknown mechanisms (McHutchison, J G, et al. *N. Engl. J. Med.* 339(21): 1485–92, 1998; Davis G L, et al. *N. Engl. J. Med.* 339(21): 1493–9, 1998; Poynard T., et al., *Lancet* 352(9138): 1426–32, 1998; Brown, J L, *Lancet* 351(9096): 78–9, 1998).

IL-2 Therapy in Hepatitis

IL-2 has been used as therapy in both HBV and HCV. In HBV, IL-2 was used in doses of $9 \times 10^6$ Chiron Units (CU) subcutaneously once per week for three weeks, followed by $1.8 \times 10^6$ CU twice a week for three months (Tilg, H. et al., *J. Hepatol.* 19(2): 259–67, 1993). There was a 50% reduction in HBV viral titer in 4/7 subjects, with no subjects conpletely clearing the virus. The decrease in viral titer was accompanied by a transient 30% increase, followed by a 30% decrease, in ALT levels.

In a second study of HBV, IL-2 doses up to $3.6 \times 10^6$ CU/day SC qd for eight weeks were given, with a response seen in 5/30 subjects (Artillo, S., et al. *J. Med. Virol.* 54(3): 167–72, 1998). There was no flare in ALT levels preceding the resolution of the hepatitis.

In a phase I dose finding/safety trial of the use of IL-2 in HCV, 33 subjects were treated with IL-2 at subcutaneous doses ranging from $0.9 \times 10^6$ to $3.6 \times 10^6$ CU qd daily five days per week. The dose found to be best tolerated and most effective was $2 \times 10^6$ CT/day. Therapy was continued for 12 weeks, and no IFN was given concomitantly. Neither toxicity and nor a flare of hepatitis were associated with this study. There was a statistically significant decrease in ALT, and a decrease in viral RNA which was not statistically significant (Pardo, M., et al. *C. Hepatology*, 26(5): 1318–21, 1997). At the preferred dose, there was a 24% biochemical response rate as defined by normalization of ALT at the end of treatment, and a 12% biochemical response rate 6 months following a 12 week course of therapy. No sustained virologic response was found.

Two trials of the use of IL-2 in dual HCV/HIV infection have been reported, thus far only in abstract form. In one report, in doses not specified, there was a decrease in both HCV viral load and ALT (Sclaak, J., et al., *Hepatology* 28(4): 507A, 1998). A second study reported that 1–2 MIU of IL-2 subcutaneously daily resulted in a decrease in HCV viremia, and 70 percent of subjects showed a decrease in ALT (DeBona, A. et al, *Hepatology* 28(4): 475A, 1998).

Combination therapy with IL-2 and IFN-α has been used extensively in malignancies (Atzpodien, J., et al., *Lancet* 335(8704): 1509–12, 1990; Budd, G T et al., *Cancer Res.* 49(2): 6432–6, 1989; Schneekloth, C., et al., *Acta Haematol.* 89(1): 13–21, 1993; Canobbio, L., et al., Anticancer Res. 16(1): 541–4, 1996; Anon, *Viral hepatitis surveillance program* 1993. Centers for Disease Control and Prevention Report #56). In these situations, there are increases in NK cells, NK killing ability, and absolute numbers of lymphocytes. This combination of cytokine anti-tumor therapy has been effective in some cases of renal cell carcinoma and metastatic melanoma.

Although long term low-dose cytokine therapy has been found to effectively improve immune function in conjunction with antiviral therapy there have not been any reports on the administration of cytokines to immune impaired infants or mammalian animals, to individuals after having antiviral therapy, or to normal individuals, infants or mammalian animals which may be temporarily afflicted with an infection or other condition, and who would benefit from a stimulation, enhancement or restoration of their immune system to overcome the condition.

It is an object of the present invention to provide a treatment regimen to accelerate the recovery of the immune system after discontinuation of anti-viral treatment without systemic toxicity such that the occurrence of relapse of infection will be inhibited or decreased.

It is a further object of the invention to provide a method of enhancing the immune system of a subject without systemic toxicity such that an individual is protected from potential viral or other infectious agent challenge.

SUMMARY OF THE INVENTION

The present invention provides a method for the potentiation of an immune response to an infection after the discontinuation of treatment for the infection prior to vaccination against the infection. This method comprises administering to a subject a composition comprising Interleukin-2 (IL-2) in an amount effective to maintain immune enhancement without eliciting toxicity of Grade 1 or higher, as defined by the World Health Organization.

The method of the present invention facilitates the prevention of relapse and or alleviates the severity of relapse of the immune system when again exposed to viral infection. This method also reduces or prevents the reoccurrence of viral infections due to lack of containment of latent virus or resumption of replication of previously latent virus.

In a preferred embodiment the invention provides a method of potentiating immune function following the discontinuation of antiviral drug therapy by administering IL-2 at a dose effective to improve immune function. In a further aspect of this embodiment the antiviral therapy is augmented with low dose IL-2 therapy.

IL-2 is suitable for the restoration or augmentation of immune response in a subject when administered at a dose effective to saturate IL-2 receptors and restore lymphocyte counts to normal levels. The amount of IL-2 administered may be determined as described herein, and is preferably about 100,000 to about 500,000 IU IL-2/m$^2$ body surface/day. The present immunotherapy is useful for potentiating the immune system to prevent infection (by improving the efficacy of vaccination) and to prevent reinfection by latent virus, particularly HIV and HCV.

In another embodiment, the method of the present invention provides a method of potentiating immune function during antiviral therapy, for example in combination with IFN-α and ribavirin in treating HCV.

To identify activated cells, whole blood (1 ml) was cultured for 18 hours with the co-stimulatory antibodies anti-CD28 and anti-CD49d, and HIV p24 antigen (1 μg/ml, Research Diagnostics, Inc., Flanders N.J.) and cytomegalovirus antigen (1 μg/ml, Advanced Biotechnologies, Columbia, Md.). At the end of the incubaton the erythrocytes were lysed using FACSLysing Solution™ (9 ml). The cells were then either frozen at −70° C. in 2 ml RPMI 1640 medum with 10% Dimethyl Sulfoxide (Sigma, St. Louis, Mo.) or permeabilized with FACSPerm Solution™ (2 ml). Thereafter the cells were reacted with anti-CD3-PerCP, anti-CD4-PE, anti-CD8-PE, anti-CD56-PE, anti-CD69-FITC, anti-CD25-FITC, and anti-IFN-γ-FITC. All antibodies were from Becton Dickinson. Preliminary experiments revealed that none of 20 control individuals who were HIV antibody negative reacted with HIV p24 antigen by expressing activation markers.

Figure 5:
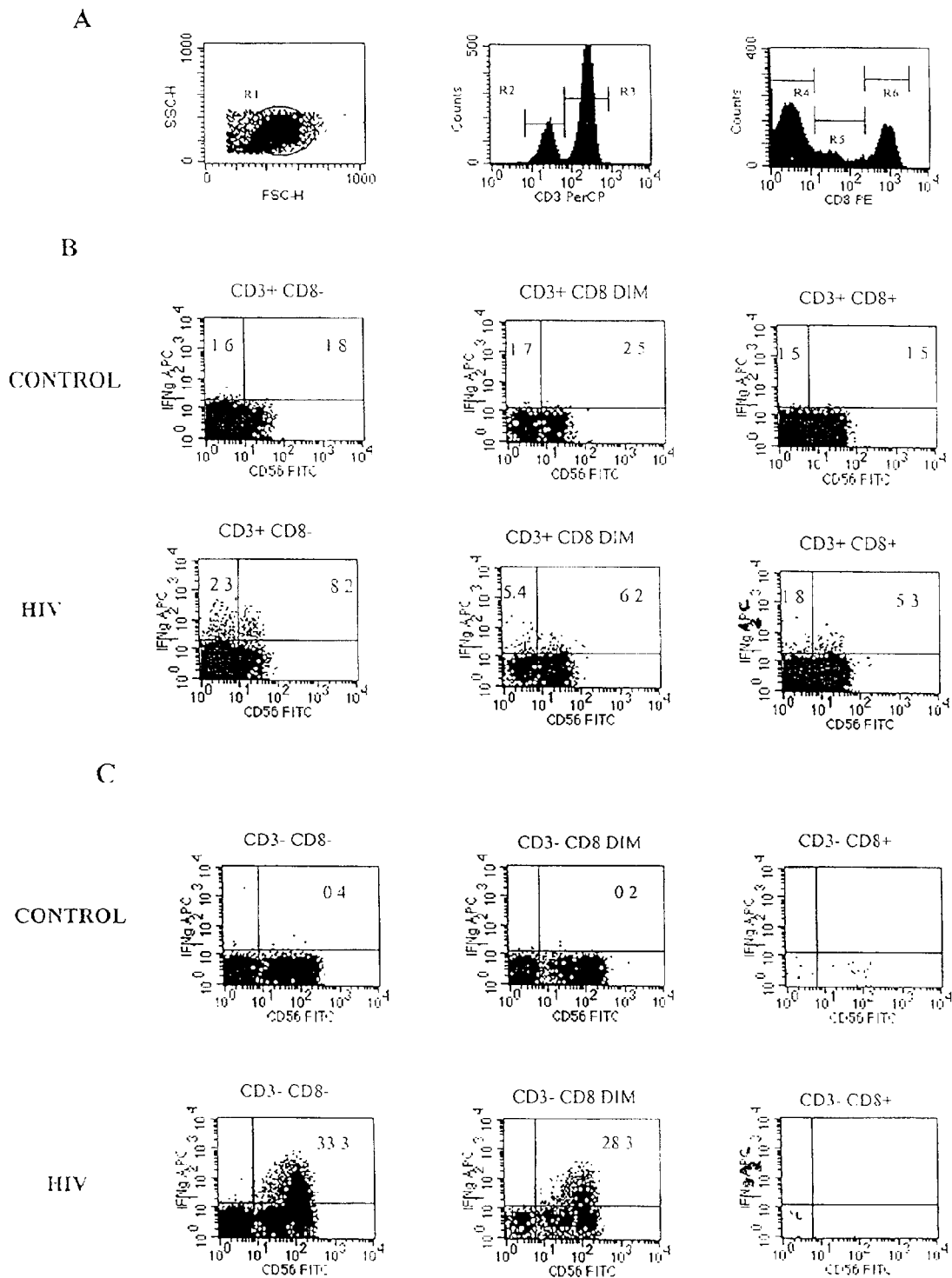

FIG. 5 Expression of interferon γ (IFN-γ) by CD-3+ and CD3− lymphocytes. A. Cells examined for size and granularity (left panel), CD3 expression (middle panel), and CD8 expression (right panel). B. Expression of IFN-γ and CD56 by CD3+ cells (gate R2), according to CD8− cells (gate R4, left panels), CD8 dim (gate R5, middle panels), and CD8+ (gate R6, right panels). Control cultures stimulated only with accessory antibodies (upper panels, HIV p24-stimulated cultures (lower panels). C. Expression of IFN-γ and CD56 by CD3− cells (gate R3), according to CD8− cells (gate R4, left panels), CD8dim (gate 5, middle panels) and CD8+

(gate R6, right panels). Control cultures stimulated only with accessory antibodies (upper panes, antiCD28, CD49d), HIV p-24-stimulated cultures (lower panels). Numbers in upper quadrants represent the percentages of CD56− and CD56+ cells that also reacted with anti-IFN-γ. To examine the activation of T cells and NK cells together, the cells were reacted with anti-CD3-PerCP, anti-CD8-PE, and anti-CD56-FITC, together with anti-IFN-γ-APC, all from Becton Dickinson.

DETAILED DESCRIPTION OF THE INVENTION

The present invention is based, in part, on the discovery that low doses of IL-2, preferably on a daily basis, further restore immune function after cessation of successful treatment with antiviral agents. The present invention is based in part on applicant's discovery that it is possible to discontinue Highly Active Antiviral Therapy (HAART) for HIV, while maintaining low dose IL-2 stimulatory therapy such that the IL-2 repairs and stimulates immune reactivity and thus is able to contain the virus and maintain latency. Highly Active Antiviral Therapy (HAART) and Potent anti-viral therapy (PART) are both used herein to describe and mean combination antiviral HIV therapy with protease inhibitors (PI) and reverse transcriptase (RT) inhibitors.

These results were unexpected in that until now it was assumed that if virus replication was allowed to resume upon discontinuation of PART, the plasma virus concentration would increase to a reach a plateau. Until now, the idea that host defenses could play an active role in determining the concentration of circulating virus has not been considered.

The term IL-2, as used herein, refers to natural and recombinant IL-2, active fragments, pharmaceutically acceptable analogues, derivatives thereof, and mixtures thereof, in amounts effective to activate their respective high affinity cytokine receptors. For purposes of the present invention suitable agents having IL-2 activity can include but are not limited to natural and recombinant forms of IL-2, IL-2 fusion proteins, and PEG, carbohydrate, lipid, therapeutic agent, reduced, non-glycosylated, and mutated derivatives thereof, and pharmaceutically acceptable analogues and derivatives thereof, and mixtures thereof, where a dose of about 1,000 pmole/m$^2$ yields a peak plasma concentration about 20 pM 2 hours after a subcutaneous injection.

Throughout this patent, where possible, all reported cytokine units of biological activity have been converted to International Units (IU) to enable a comparison of the doses of the same cytokine used in different studies. Also, where possible, and when appropriate, cytokines will be referred to as the amount of protein, in weight or moles for uniformity's sake. In addition, some agents' doses are expressed as either IU or moles per m$^2$ of body surface area (BSA). The BSA values are easily calculated from similar values based on a subject's weight and height using a standard conversion table of height and weight measurements. For example, a 70 kg person of normal height has about 1.5 m$^2$ BSA.

In accordance with the invention, IL-2 is administered at a low dose, without eliciting substantial toxicity WHO grade 1 or higher. The safe, non-toxic use of cytokines relies on information regarding cytokines' binding to high affinity specific receptors, and is determined using the principles described in U.S. patent application Ser. No. 08/608,516, WO97/03306, 08/646,098 and PCT/US97/07787. Some of the toxicities which are monitored to determine a suitable dosage for the agent utilized in the studies include weakness, fatigue, lethargy, myalgia, and low grade fever. These symptoms usually occur within a few days after beginning the agent's administration. When toxicity is observed during a trial, therapy should be immediately stopped, and the patients placed on a lower daily dose of the agent. If necessary, this procedure is repeated until a safe dose is found. It is contemplated that the present immunotherapy is effective and free of toxicity WHO grade 1 or higher for periods greater than about 6 months or 1 year, and even for longer periods of time, without producing systemic side effects or significant laboratory abnormalities.

The administration of low doses of the agent of this invention, as described herein, result in stimulation of the immune system, which is evidenced by and may be determined by measuring changes in levels of NK cells, eosinophils, monocytes, and/or CD4+ T-cells, among others. The substantially lower cytokine doses utilized herein, when administered continuously, produce an increase in one or more groups of circulating immunity-building cells such as lymphocytes, monocytes and polymorphonuclear lymphocytes, including T-cells, particularly CD4+ T-cells, B-cells, natural killer (NK), eosinophils, monocytes, basophils, and antigen-presenting cells. Significant stimulation of the immune system is indicated by substantial increases in circulating leukocytes, such as NK cells, eosinophils, monocytes, and/or CD+4 T-cells, among others.

"Immune potentiation" as used herein is defined as enhancement of the ability of the immune system to mount an effective immune response. Immune potentiation with low-dose IL-2 therapy maintains the high levels achieved in immune restoration with antiviral, i.e., increased numbers of CD4+ T cells, CD8+ T cells and circulating NK cells.

Post-Antiviral Immune Potentiation

Accordingly, in one aspect of the invention the invention provides for treating a subject who has had successful treatment with antiviral agents with IL-2 in an amount effective to achieve and maintain immune enhancement or "potentiation".

In another aspect of the invention, in addition to treatment with HAART, the subject may also have been treated with low dose IL-2 therapy. Upon discontinuation of HAART, IL-2 administration is continued in an amount effective to maintain the restoration of the immune system.

Successful antiviral therapy is seen in those subjects who have achieved remission, i.e. had undetectable plasma viral RNA levels for at least three months and/or those who have received at least three months of low-dose IL-2 therapy and have been immune enhanced. Immune enhancement is defined by a normal concentration of circulating CD4+ T cells with elevated CD8+ T cells and elevated Natural Killer (NK) cells beyond the normal range.

For individuals infected with HIV, the low dose of the agent administered in accordance with this invention, either in combination with antiviral therapy or after cessation of therapy, does not stimulate viral production (e.g., HIV), as reported previously with i.v. administration of high IL-2 doses. Moreover, viral replication is suppressed by the immune system when IL-2 is administered daily in low doses after the cessation of the antivirals. Further, no opportunistic infections or malignancies are observed in any of the individuals receiving the low doses of agent of this invention.

The combination of low dose IL-2 therapy with standard antiviral therapy (INF-α and ribavirin) in individuals infected with HCV activates the immune system while simultaneously decreasing the viral load and in fact increases the sustained viral response rate over that obtained with standard therapy alone. Low dose IL-2 therapy augments both NK and HCV antigen specific CTL which may have therapeutic benefit in HCV infection.

The term "viral load" is used herein to refer to a quantitative amount of virus in an animal. Infectivity can be evaluated either by detecting virus, i.e., viral load, or by observing disease progression in the animal. Virus (viral load) can be detected by the presence of viral nucleic acids, e.g., detected by PCR or RT-PCR or direct hybridization techniques. In a specific embodiment, detectable plasma viral RNA is defined as greater than 1,000 RNA molecules/ml by the branched chain DNA (bDNA) assay (LLD of 50 molecules/ml), (Jacobsen, E L et al., Proc Natl Acad Sci USA 3:10405–10, 1996). It can also be detected, if present in sufficient amount, by the presence of viral proteins, e.g., detected by immunoassay or biochemical techniques. Alternatively, extracts from tissue samples from the animal are used to infect cells in culture; the presence of virus is detected by development of CPE. Pathogenicity is evaluated by gross examination of symptomology of the animal, such as fever, fatigue, discoordination, convulsions, and other neurological symptoms, diarrhea, hemorrhage, mortality, etc. (see, Thiel et al., Fields Virology, Third Edition, edited by B. N. Fields et al., Chapter 33, pp. 1059–1073, 1996). Either evaluation can be part of an acute condition, i.e., arising and resolving over a short period, or a chronic condition, i.e., persisting for a long period of time.

Vaccine Augmentation

The invention also provides for immunoprotection of the immune system in conjunction with administration of a vaccine. Accordingly, low dose IL-2, as set forth herein, can be commenced in advance of vaccine administration. The low dose IL-2 treatment can continue at the time of, and subsequent to, vaccination.

As used herein, the term "vaccine" refers to a vaccine comprising an immunogen from an infectious pathogen and, generally, an adjuvant. The term "vaccine" refers to a composition (protein or vector; the latter may also be loosely termed a "DNA vaccine", although RNA vectors can be used as well) can be used to elicit protective immunity in a recipient. It should be noted that to be effective, a vaccine of the invention may elicit immunity in a portion of the population, as some individuals may fail to mount a robust or protective immune response, or, in some cases, any immune response. This inability may stem from the individual's genetic background or because of an immunodeficiency condition (either acquired or congenital) or immunosuppression (e.g., treatment with immunosuppressive drugs to prevent organ rejection or suppress an autoimmune condition). Advantageously, low dose IL-2 immunopotentiation directly addresses the latter problem, and may improve the former as well. Efficacy can be established in animal models.

An "adjuvant" is a molecule or composition that potentiates the immune response to an immunogen. An adjuvant is "acceptable for use in a human" when it is pharmaceutically acceptable, as defined below. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful human adjuvants such as but not limited to alum, BCG (bacille Calmette-Guerin) and *Corynebacterium parvum*. An example of a preferred synthetic adjuvant is QS-21.

The term "protect" is used herein to mean prevent or treat, or both, as appropriate, a viral or other infection in a subject. Thus, prophylactic administration of the vaccine can protect the recipient subject from viral infection, e.g., to prevent infectious mononucleosis or lymphoproliferative diseases. Therapeutic administration of the vaccine or immunotherapy can protect the recipient from recurrence of HIV or HCV-infection-mediated pathogenesis, i.e., the target for the discontinued antiviral therapy.

The term "subject" as used herein refers to an animal that supports a viral infection. In particular, the term refers to a human.

The term "DNA vaccines" is an informal term of art, and is used herein to refer to vaccines delivered by means of a recombinant vector. An alternative, and more descriptive term used herein is "vector vaccine" (since some potential vectors, such as retroviruses and lentiviruses are RNA viruses, and since in some instances non-viral RNA instead of DNA can be delivered to cells). Generally, the vector is administered in vivo, but ex vivo transduction of appropriate antigen presenting cells, such as dendritic cells, with administration of the transduced cells in vivo, is also contemplated. The vector systems described above are ideal for delivery of a vector for expression of an immunogenic polypeptide of the invention.

In another aspect, low dose IL-2 administration can potentiate immune response during immunotherapy. "Immunotherapy" refers to therapeutic treatment of a disease of infection, such as a tumor or virus, by administration of an antigen from the pathogen (tumor cell or tumor cell antigen or virus or viral protein), usually with an adjuvant.

Treatment of Infectious Diseases

The present treatment is suitable for application to a variety of conditions, which benefit from the stimulation and/or inhibition of the immune system. As used herein, the term "infectious disease" includes diseases and disorders that result from viral or bacterial infection. It further includes parasite infestation. In addition, for purposes of the present invention as it relates to immunotherapy, the term "infectious disease" includes cancer.

Pharmaceutical Compositions

Low dose IL-2 is preferably formulated as a pharmaceutical composition with a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Sterile water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. Certain adjuvants mentioned above, particularly mineral oils and adjuvants containing mineral oils (e.g., Freund's adjuvant) are not acceptable for use in humans.

Parameters that may be monitored in order to adjust the dose of the agent administered daily are the blood cell count of circulating lymphocytes, monocytes and polymorphonuclear leukocytes, such as T-cells, B-cells, NK cells, monocytes, eosinophils, neutrophils, basophils, antigen-presenting cells, among others. In the case of viral infections, particularly in the presence of the human immunodeficiency virus, one of the ways to determine an adjustment in the dose administered to an individual is to monitor the count of circulating microorganisms.

Different preparations of a specific cytokine or related agent, and different formulations may require varied daily doses, which depend on the agent's binding constant to the respective receptors, and the existence and number of different kinds of receptors they selectively bind to. These values may be determined utilizing a ligand-receptor binding assay. The ligand-receptor binding assay may be conducted, for the different agents in accordance with this invention, as described by Robb et al., *J. Exp. Med.* 154: 1455–1474, 1981. In brief, a cytokine such as IL-2, IL-12, IL-15, IFN-α, IFN-β, IFN-γ, the CD-40 ligand, or any other ligand (agent) in accordance with this invention, must be in their native configuration, and substantially free of contamination by other molecules. The ligand or agent may be labeled, for example, using radioisotopes, enzymes, and other markers. Target cells, isolated membranes, cytoplasm, or nuclei, may then be mixed together with the labeled ligand, and the ligand and receptor allowed to reach a steady state, where the rate of association of the ligand with the receptor about equals the rate of dissociation of the ligand from the receptor. Subsequently, any unbound ligand or agent may be separated from the receptor-bound ligand or agent, usually by centrifuging the bound ligand or agent, and the amounts of the bound and unbound ligand or agent measured. The affinity of the ligand-receptor interaction (Kd) may be calculated, as well as the number of receptors per cell, or per weight of cytoplasm or nuclei, from these two experimentally determined values, knowing the number of cells, or amount of membranes, cytoplasm, or nuclei, used.

The data may be plotted by the method described by Scatchard, *Ann. NY Acad. Sci.* 51: 660–672, 1949. The ratio of bound vs. free ligand or agent may be plotted on the y-axis and the amount of bound ligand or agent on the x axis. The slope of the data points yields the Kd (x/y), whereas the x-axis intercept yields the number of receptors. Knowing the equilibrium dissociation constant (Kd), the % receptors that will be occupied at each ligand or agent concentration may be calculated as described above.

The dosage of the agent having IL-2 activity of the present invention will further depend on the disease state or condition being treated and other clinical factors such as weight and condition of the human or animal and the route of administration of the compound.

Bioequivalent doses of IL-2 can be obtained using formulations from different sources by those with skill in the art by for example first assessing the biologic activity in vitro using the CTLL assay (Gillis, S. J., *Immunol.* 120:2027, 1978), calculating the specific activity of the formulation or performing in vivo pharmacokinetic testing to determine the potency of the formulation and determining the appropriate dosage for use in accordance with the teachings of this invention.

Prior to the studies described herein using IL-2 from Chiron (Chiron Therapeutics Inc., Emeryville Calif.), we used IL-2 from Amgen (Amgen Corporation, Thousand Oaks, Calif.). Our use of the Chiron IL-2 revealed differences in the formulations of the two products. Amgen IL-2 was formulated to an ultimate concentration of 0.4 mg/ml. in low ionic strength sodium acetate buffer (10 mM), pH 4, while Chiron IL-2 was formulated at 1.1 mg/ml, in phosphate buffer at physiological ionic strength (150 mM) and pH 7. This formulation of the Chiron product rendered it less soluble, and the ionic detergent sodium dodecyl sulfate (SDS) was added to the preparation. The Chiron formulation was approximately 6-fold less than the Amgen preparation, due to the decreased available protein concentration in the Chiron preparation.

Initial studies comparing the biological activity showed significant differences between the products (see Examples). In vivo bioavailability studies confirmed that a 5-fold higher dose of Chiron IL-2 on a weight/weight basis provided the same amount of bioavailable IL-2 as obtained in the Amgen IL-2. We also confirmed that administration of higher amounts by weight of Chiron IL-2 did not adversely affect patients i,.e., did not produce toxic side effects.

The methods of the present invention contemplate single as well as multiple administrations given either simultaneously or over an extended period of time. Given that 1 pmole IL-2 is equivalent to about 250 IU, preferred daily doses of IL-2 are about 15,000 and lower, to about 1,500,000 IU and higher, preferably up to about 1,000,000 IU, more preferably up to about 750,000 IU, and still more preferably up to about 500,000 IU, and as low as about 20,000 IU, preferably as low as about 50,000 IU, and still more preferably as low as about 60,000 IU, and equivalent amounts of its pharmaceutically acceptable analogues and derivatives thereof, or mixtures thereof. In a preferred embodiment, about 100,000 to about 500,000 IU IL-2/$m^2$ body surface/day or the equivalent is administered.

A useful form of the invention is a unit dosage composition, which may be packaged in a sterile container, having sufficient amounts of one or more forms of the agent to maintain a therapeutic level in blood for a period of about 24 hours. This amount of the agent to be administered may be calculated as described above for each individual agent. The agent may be self-administered by the human subject, preferably subcutaneously, transdermally, intrapulmonarily, transbuccally, or by implant. However, for specific types of patients or applications other forms are also preferred.

The unit dosage composition may be prepared in a variety of forms for the delivery of the agent. Examples are powder, tablet, capsule, dragee, cream, solution, suspension, emulsion, gel, spray, or liposomal or other micellar forms. Preferred are solid, particularly freeze-dried, and liquid forms. Also preferred are other forms such as those suitable for injection, topical application, controlled release products, inhalation, and others. Examples of controlled release products are transdermal and intradermal devices, slow release oral formulations, patches, skin, mucosal and transbuccal implants, suppositories, and the like. Implants are preferred for long term delivery of the agent. Controlled release products may be prepared as is known in the art and designed for releasing desired amounts of the agent over a predetermined period of time. In most instances, the amount of the agent contained in the control release product is substantially higher than the desired daily dose. In some cases, the product may contain sufficient amounts of agent for releasing a daily dose over a period of days, weeks, months, and even years. The product may be tested, and the amount of agent to be released adjusted in accordance with the observed absorbed dose. Any of the forms for administration of the agent may also contain other formulation components.

Various forms of the composition are provided herein for administration of the agent of the invention under the conditions prescribed herein. One of them is a systemic composition, also comprising a diluent and/or carrier for system administration, and optionally other additives which are described below or standard in the art. This form may be in the form of a solution, suspension, powder, tablet, an emulsion, and encapsulated particles, among others, or mixtures or combinations of these forms. The agent may be present in the systemic composition in an amount of about 0.0001 to 50 wt % of the composition, more preferably about 0.1 to 30 wt %.

Another form is a topical composition, which in addition to the agent comprises a carrier or diluent for the agent, which is suitable for its transdermal delivery and optionally one or more of a variety of agents suitable for the preparation of different formulations, which will be selected in accordance with the type of formulation and route of administration desired. Examples of these ingredients are buffers, salt forming acids and bases, perfumes, colorants, emollients, adjuvants, single or multiple enteric coatings, copolymers, microporous or semi-permeable membranes, enzyme inhibitors, mucoadhesives, chelating agents, particulate systems, viral envelope proteins, liposomes and other micelles, emulsifiers, lipoproteins and other fatty acid derivatives, surfactants, bile salts, hydrophilic, neutral, and hydrophobic polymers and co-polymers, hydrogels, biodegradable polymers and co-polymers. The composition may also contain additional bioactive agents such anti-bacterial, anti-viral, anti-fungal, anti-parasitic, anti-metabolic, anti-inflammatory, vasoactive, anti-neoplastic, bronchodilating, local anesthetic, immunomodulating, growth promoting and regenerating agents, enzymatic, hormonal agents, neurotransmitters, and cell receptor proteins and ligands. This composition may be in the form of a cream, an ointment, a solution, a gel, a powder, a suspension, an emulsion, encapsulated particles, or mixtures or combinations of these forms. The agent may be present in different amounts, typically the dermal composition has about 0.001 to 50 wt % or more, and preferably about 0.1 to 30 wt %. However, other amounts larger and smaller are also suitable. Another preferred form of the composition is in the form of a controlled release composition wherein the formulation ingredients added control the rate of release of the agent. These may be degradable polymers and copolymers, matrixes which "leach out" the agent, and the like, as is known in the art.

The additional ingredients, which are optionally present in the composition are generally utilized in amounts standard in the art.

The composition may be produced in the form of an implant, including an encapsulated recombinant cell implant (cytotherapeutics), for releasing a desired amount of the agent over a pre-determined period of time. Any and all compositions in accordance with the invention may also be provided as a kit, along with instructions for its use, particularly in terms of the any necessary manipulations, the number, frequency, and timing of administrations or applications, the form or area of the body to be applied to, taking into consideration different body surface area and weight of the subject. This is particularly important when it is applied or administered to children, particularly infants and newborn babies, the infirm, and the elderly, as well as to small and large animals. Smaller or larger doses may be required in these cases.

The composition may be delivered from a passive transdermal delivery device formed from a solid support with a compartment containing a solution or suspension comprising the composition. The compartment has a permeable side which is applied to an area of a subject's skin or dermis and the agent is allowed to pass from the device onto and through the skin, mucosal, or buccal surfaces of the subject. The device is preferably placed in a sealed sterile container immediately after manufacture by methods known in the art. A removable cover may be placed on the permeable side of the container prior to sealing and/or packaging to retain the solution or suspension of the agent during storage and prior to use.

This device may be in the form of an electrotransport device which also contains donor and counter electrodes, an external power source and control circuitry. This device may also be in the form of ultrasound device also containing an ultrasound generator or transducer, an external power source, and control circuitry. Such devices are known in the art and need not be further described herein. The solution or suspension containing the agent requires the presence of electric conducting agents which will aid in the transport of the electrical current which facilitates the passage of the agent from the solution onto the skin or dermis and through it. In the case of protein such as the present agent, it becomes important to provide means of administration that will not degrade or hydrolyze the peptic bonds, in order to preserve the activity of the agent In this respect, the topical application of the agent in the form of a multiplicity of formulations is ideally suited to avoid the hydrolyzing conditions of the gastrointestinal tract while providing a direct passage, after the agent is absorbed through the skin or mucous tissue, directly into the blood stream.

The agent of this invention may also be administered from an inhalant device, including those utilized to introduce therapeutic or preventative agents into the lungs, as is the case of transpulmonary administration to asthmatic patients. Such devices are known in the art and available commercially. All types of products and compositions which are part of this invention may be provided as a kit, and preferably as a self-administration kit, primarily comprising, in separate sterile containers, a number of unit dosage compositions, and detailed instructions for use of the kit, and optionally, one or more devices including syringes and needles, transdermal, transbuccal, or intradermal patches or implants, or inhalators, for delivering the agent, and a carrier diluent. These devices may be placed in sterile containers, and the entire kit may be contained in a case for marketing and distribution.

Low Dose IL-2 Gene Therapy

It is also contemplated that IL-2 can be delivered to a subject using cells engineered to produce and secrete IL-2 or agents having IL-2 activity. Accordingly, the present invention contemplates various cloning and expression vectors for expression of IL-2 or polypeptide having IL-2 activity. Such expression vectors can be used to transform cells in vitro.

The coding sequence for such a polypeptide may, and preferably does, include a signal sequence, which can be a heterologous signal sequence, e.g., for optimized signal sequence processing in a bacterial, yeast, insect, or mammalian cell. The term "signal sequence" is used herein to refer to the N-terminal, hydrophobic sequence found on most secreted proteins that identifies it for processing for secretion from the cell. Generally, the signal sequence is cleaved during processing. However, various constructs of the invention can include a partial signal sequence. It is not necessarily the case that the partial signal sequence is processed normally, or that it even provides for translocation during expression, e.g., to the bacterial periplasm.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et at., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. 1985); *Transcription And Translation* (B. D. Hames & S. J. Higgins, eds. 1984); *Animal Cell Culture* (R. I. Freshney, ed. 1986); *Immobilized Cells And Enzymes* (IRL Press, 1986); B. Perbal, *A Practical Guide To Molecular Cloning* (1984); F. M. Ausubel et al. (eds.), *Current Protocols in Molecular Biology*, John Wiley & Sons, Inc. (1994).

Molecule Biology Definitions

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The coding sequences herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'- non-coding regions, and the like.

The term "gene", also called a "structural gene" means a DNA sequence that codes for or corresponds to a particular sequence of amino acids which comprise all or part of one or more proteins, and may or may not include regulatory DNA sequences, such as promoter sequences, which determine for example the conditions under which the gene is expressed.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art.

The term "vector for expression in humans" as used herein means that the vector at least includes a promoter that is effective in human cells, and preferably that the vector is safe and effective in humans. Such a vector will, for example, omit extraneous genes not involved in developing immunity. If it is a viral vector, it will omit regions that permit replication and development of a robust infection, and will be engineered to avoid development of replication competence in vivo. Such vectors are preferably safe for use in humans; in a more preferred embodiment, the vector is approved by a government regulatory agency (such as the Food and Drug Administration) for clinical testing or use in humans.

Expression Vectors

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. Nos. 5,385,839 and 5,168,062), the SV40 early promoter region (Benoist and Chambon, Nature 290:304–310, 1981), the promoter contained in the 3' long terminal repeat of Rous sarcoma virus (Yamamoto, et al., Cell 22:787–797, 1980), the herpes thymidine kinase promoter (Wagner, et al., Proc. Natl. Acad. Sci. U.S.A. 78:1441–1445, 1981), the regulatory sequences of the metallothionein gene (Brinster, et al., Nature 296:39–42, 1982); prokaryotic expression vectors such as the b-lactamase promoter (Villa-Komaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also "Useful proteins from recombinant bacteria" in Scientific American, 242:74–94, 1980; promoter elements from yeast or other fungi such as the Gal 4 promoter, the ADC (alcohol dehydrogenase) promoter, PGK (phosphoglycerol kinase) promoter, alkaline phosphatase promoter; and control regions that exhibit hematopoietic tissue specificity, in particular: immunoglobin gene control region, which is active in lymphoid cells (Grosschedl et al., Cell, 38:647, 1984; Adames et al., Nature, 318:533, 1985; Alexander et al., Mol. Cell Biol., 7:1436, 1987); beta-globin gene control region which is active in myeloid cells (Mogram, et al., Nature 315:338–340, 1985; Kollias, et at., Cell 46:89–94, 1986), hematopoietic stem cell differentiation factor promoters; erythropoietin receptor promoter (Maouche, et al., Blood, 15:2557, 1991), etc; and control regions that exhibit mucosal epithelial cell specificity.

Preferred vectors, particularly for cellular assays in vitro and vaccination in vivo or ex vivo, are viral vectors, such as lentiviruses, retroviruses, herpes viruses, adenoviruses, adeno-associated viruses, vaccinia viruses, baculoviruses, and other recombinant viruses known to those skilled in the art with desirable cellular tropism. Thus, a vector encoding IL-2 can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and vaccination procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Examples of particular vectors include, but are not limited to, a defective herpes virus 1 (HSV1) vector (Kaplitt, et al., Molec. Cell. Neurosci. 2:320–330, 1991; International Patent Publication No. WO 94121807, published Sep. 29, 1994; International Patent Publication No. WO 92/05263, published Apr. 2, 1994); an attenuated adenovirus vector, such as the vector described by Stratford-Perricaudet, et al. (J. Clin. Invest. 90:626–630, 1992; see also La Salle, et al., Science 259:988–990, 1993); and a defective adeno-associated virus vector (Samulski, et al., J. Virol. 61:3096–3101, 1987; Samulski, et al., J. Virol. 63:3822–3828, 1989; Lebkowski, et al., Mol. Cell. Biol. 8:3988–3996, 1988).

The gene can be introduced in a retroviral vector, e.g., as described in Anderson, et al., U.S. Pat. No. 5,399,346; Mann, et al., 1983, Cell 33:153; Temin, et al., U.S. Pat. No. 4,650,764; Temin, et al., U.S. Pat. No. 4,980,289; Markowitz, et al., 1988, J. Virol. 62:1120; Temin, et al., U.S. Pat. No. 5,124,263; EP 453242, EP178220; Bernstein, et al. Genet. Eng. 7 (1985) 235; McCormick, BioTechnology 3 (1985) 689; International Patent Publication No. WO 95/07358, published Mar. 16, 1995, by Dougherty, et al.; and Kuo, et al., 1993, Blood 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (WO 90/02806) and the GP+envAm-12 cell line (WO 89/07150). In addition, the recombinant retroviral vectors can contain modifications within the LTRs for suppressing transcriptional activity as well as extensive encapsidation sequences which may include a part of the gag gene (Bender, et al, J. Virol. 61:1639, 1987). Recombinant retroviral vectors are purified by standard techniques known to those having ordinary skill in the art.

Retrovirus vectors can also be introduced by DNA viruses, which permits one cycle of retroviral replication and amplifies tranfection efficiency (see WO 95/22617, WO 95/26411, WO 96/39036, WO 97/19182).

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. U.S.A. 84:7413–7417, 1987; Felgner and Ringold, Science 337:387–388, 1989: see Mackey, et al., Proc. Natl. Acad. Sci. U.S.A. 85:8027–8031, 1988; Ulmer, et al., Science 259:1745–17, 1993). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

Alternatively, non-viral DNA vectors for gene therapy can be introduced into the desired host cells by methods known in the art, e.g., electroporation, microinjection, cell fusion, DEAE dextran, calcium phosphate precipitation, use of a gene gun (ballistic transfection; see, e.g., U.S. Pat. No. 5,204,253, U.S. Pat. No. 5,853,663, U.S. Pat. No. 5,885,795, and U.S. Pat. No. 5,702,384 and see Sanford, TIB-TECH, 6:299–302, 1988; Fynan et al., Proc. Natl. Acad. Sci. U.S.A., 90:11478–112, 1993; and Yang et al., Proc. Natl. Acad. Sci. U.S.A., 87:1568–9572, 1990), or use of a DNA vector transporter (see, e.g., Wu, et al., J. Biol. Chem. 267:963–967, 1992; Wu and Wu, J. Biol. Chem. 263:14621–14624, 1988; Hartmut, et al., Canadian Patent Application No. 2,012,311, filed Mar. 15, 1990; Williams, et al., Proc. Natl. Acad. Sci. USA 88:2726–2730, 1991). Receptor-mediated DNA delivery approaches can also be used (Curiel, et al., Hum. Gene Ther. 3:147–154, 1992; Wu and Wu, J. Biol. Chem. 262:4429–4432, 1987). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir, et al., C.P. Acad. Sci., 321:893, 1998; WO 99/01157; WO 99/01158; WO 99/01175).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all sizes and all molecular weight or molecular mass values are approximate, and are provided for description.

Patents, patent applications, procedures, and publications cited throughout this application are incorporated herein by reference in their entireties.

The invention will be better understood by reference to the following Examples, which are intended to illustrate the invention and are not limiting thereof.

EXAMPLES

Example 1

Comparison of IL-2 Formulations

The following experiments were performed to assess the relative characteristics of an IL-2 formulation (Proleukin) obtained from Chiron Corporation, Emeryville, Calif., and one obtained from Amgen, Thousand Oaks, Calif.

Amgen vs. Chiron Formulation Contents

The Amgen formulation contained 0.4 mg/ml IL-2 in 10 mM sodium acetate buffer pH 4. The Chiron formulation contained 1.1 mg/ml IL-2 in 150 mM phosphate buffer pH 7.

The physiologic ionic strength of the Chiron formulation, however, rendered the IL-2 less soluble than the low ionic strength of the Amgen formulation. Consequently, to better solubilize their IL-2, sodium dodecyl sulfate (SDS), an ionic detergent, was added to the Chiron formulation.

In vitro IL-2 Bioassay Results from Amgen vs. Chiron Formulations

The IL-2 Cytotoxic T-Lymphocyte Line (CTLL) bioassay was conducted as described by Gillis (Gillis, S. J. *Immunol.* 120: 2027 1978). Each of the Amgen and Chiron formulations was diluted to a concentration of 2 nM protein, were serially diluted and then added to a 96 well microtiter plate, followed by $1 \times 10^4$ CTLL cells and allowed to incubate for 24 hours. $^3$H-Thymidine was then added and the incubation continued for more hours. The incubation was stoppped, the cells harvested, and the incorporated of $^3$H-Thymidine into newly synthesized DNA detected in each sample by radioactivity counting in a beta-ray scintillation counter (Packard Instruments, Chicago, Ill.).

The results of the assay showed that the Chiron formulation was about 6-fold less potent than the Amgen preparation. Trivial explanations for the discrepancy, such as differences in protein concentration or purity of the preparations prior to dilution, were excluded by reverse phase high pressure liquid chromatography. The differences could be attributed to a decreased available protein concentration in the Chiron preparation after dilution, which was evident when the preparations were assayed for protein concentration by ELISA.

In vivo IL-2 Potency-Amgen vs. Chiron Preparations

Based upon the in vitro assay, the Chiron preparation had a 6-fold lower specific activity than the Amgen preparation. Thus, if the Amgen preparation had a specific activity of 15 million U/mg IL-2 protein, then the Chiron preparation had a specific activity of 2.5 million U/mg IL-2 protein. Accordingly, it was necessary to determine in vivo bioavailability of both preparations before proceeding with any clinical trials with the Chiron preparation.

To compare the two preparations, 4 subjects who were receiving Amgen IL-2 were asked to volunteer for PK studies. Each subject was admitted to the Cornell General Clinical Research Center (GCRC), and over successive weeks, each subject was separately administered both preparations by intravenous (i.v.) or by subcutaneous (s.q.) injection. A standard dose of Amgen IL-2 of 250,000 IU (16.7 ug)/m$^2$ was compared with a dose of Chiron IL-2 that was 5-fold higher on a weight basis (83.3 ug/m$^2$), equivalent to 250,000 IU/m$^2$ of the Chiron IL-2 based on the CTLL bioassay results.

The results revealed that the in vitro assays were predictive of the in vivo bioavailability of the two preparations, whether they were administered i.v. or subcutaneously. Accordingly, we confirmed that a dose of 1.25 million Units/m$^2$ Chiron IL-2 was equal to 250,000 Units/m$^2$ of Amgen IL-2.

Ongoing Clinical Trials of IL-2 in HIV Infection

Having satisfied ourselves that bio-equivalent doses of IL-2 could be achieved with the Chiron formulation, we have initiated a multi-center randomized, controlled trial of IL-2 in individuals who have achieved a remission of plasma virus on treatment of HAART, but who remain factor (G-CSF), granulocyte-monocyte colony stimulating factor (GM-CSF).

The parameters monitored throughout the study included the time to the onset of viremia, the rate of viremic increase, the peak plasma virus concentration and the rapidity and completeness of the disappearance of viremia. The characteristics of each subject are shown in Table I.

TABLE 1

| | | Prior to PART HIV Hx | | | Post PART + IL-2 Lymphocyte Concentration** | | |
|---|---|---|---|---|---|---|---|
| | | VL* | | PART | Mean Cells/mm3 (±SEM) | | |
| Subject # | HIV+ (years) | (RNA/ml) | CD4 Cells/mm³ | Duration (years) | CD4+ T Cell | CD8+ T Cell | NK Cell |
| 1 | 1.25 | 5,794 | 550 | 2.0 | 1296 (120) | 1155 (67) | 249 (31) |
| 2 | 2.00 | 58,000 | 389 | 2.0 | 576 (105) | 588 (41) | 365 (93) |
| 3 | 0.25 | 131,515 | 540 | 1.0 | 862 (67) | 524 (49) | 246 (46) |
| 4 | 3.67 | 8,047 | 145 | 2.5 | 563 (32) | 910 (88) | 1147 (291) |
| 5 | 0.50 | 7,656 | 250 | 1.1 | 754 (51) | 599 (61) | 376 (41) |
| 6 | 3.80 | 100,000 | 250 | 1.2 | 732 (72) | 1065 (87) | 704 (4) |
| 7 | 1.25 | 68,000 | 160 | 1.5 | 541 (91) | 569 (71) | 296 (46) |
| 8 | 4.00 | 67,821 | 380 | 3.5 | 928 (112) | 614 (41) | 321 (92) |
| 9 | 3.67 | 186,000 | 264 | 2.0 | 487 (26) | 836 (88) | 283 (67) |
| Mean | 2.26 | 70,315 | 325 | 2.0 | 748 | 762 | 443 |
| (±SEM) | (0.51) | (20,459) | 50 | (0.26) | (85) | (79) | (99) |

*Plasma HIV RNA concentrations were determined by the ultra-sensitive branched chain DNA assay (Bayer Diagnostics, Emeryville, CA) on frozen (−70° C.), EDTA anticoagulated plasma. The lower limit of detection of this assay is 50 HiV RNA molecules/ml.
**Concentration of circulating lymphocytes on HAART and low-dose IL2 therapy for the 3 months prior to cessation of HAART. Lymphocyte subsets were monitored using a FACSCalibur ™ Flow Cytometer according to the manufacturer's instructions (Becton Dickinson, San Jose, CA). Three color flow cytometry was performed using anti-CD45-PerCP to identify lymphocytes, anti-CD3-FITC to identify T cells, and anti-CD4-Pe, anti-CD8-PE, anti-CD19-PE, and anti-CD16+CD56-PEto identify the various lymphocyte subsets. All antibodies were from Becton Dickinson. Values shown are the mean ± SEM of 4 separate determinations made 1 month apart. Normal values: CD4+ T cells, mean = 895 cells/mm³, range 588–122 cells/mm³; CD8+ T cells, mean = 533 cell/mm³, range 394–672 cells/mm³; NK cells, mean = 289 cell/mm³, range 94–484 cell/mm³.

immunodeficient, with less than 300 circulating CD4+ T cells. This study is directed toward determining whether IL-2 immunostimulation can promote immune reconstitution, so that the concentration of CD4+ T cells can be returned to normal, i.e. about 900 cells/mm³. Thus far, almost 100 subjects have been entered on study.

Example 2

Effect of IL-2 After Cessation of HAART

This study was directed toward HIV-positive individuals who received HAART and achieved remission, i.e., undetectable plasma viral RNA, for at least 3 months; and received at least 3 months of low-dose IL-2 therapy and have been immune enhanced.

EXPERIMENTAL DESIGN Step I: IL-2 Therapy: Criteria for patient eligibility included a) evidence of HIV infection by serology; b) undetectable plasma HIV by bDNA @ LLD less than 50 copies/ml on 2 successive assays within 3 months; c) no history of viral detection while on HAART; and d) the patients received HAART plus IL-2 therapy for 3 months or more and never received monotherapy. Conditions for patient exclusion included a) uncontrolled infection; b) concurrent therapy with glucocorticoids or other immunosuppressive agents; or c) concurrent immunomodulating agents, eg. IFN-a, granulocyte colony stimulating All subjects had been chronically infected with HIV, with a mean time of positive HIV serology of 2.26±0.5 (SEM) years (range 0.25–4.0 years) before starting PART. The mean plasma virus concentration prior to institution of PART was 70,315±20,459 (SEM) RNA molecules/ml (range 5,794–186,000 RNA molecules/ml). Prior to the discontinuation of anti-viral therapy, the average duration of PART was 2.0±0.25 (SEM) years (range 1.0–3.5 years). At the time of PART discontinuation, the circulating CD4+ T cells were within the normal range (mean 748±85 SEM cells/mm3), while both CD8+ T cells (mean 762±79 SEM cells/mm3) and NK cells (mean 443±99 SEM cells/mm3) were elevated compared with normal ranges.

Prior to the discontinuation of PART, at least 3 months of daily, low-dose (250,000 U/m$^2$) subcutaneous IL-2 (R-Met-HU IL2-Ala-125, Amgen, Thousand Oaks, Calif.) immunostimulatory therapy were administered as described in Jacobsen, E L et al., *Proc Natl Acad Sci USA* 93:10405–10 (1996). In addition, to ensure the safest possible immune parameters for the discontinuation of PART, IL-2 immunostimulation was continued after the anti-viral drugs were withdrawn. Prior to the discontinuation of PART, plasma virus concentrations were monitored monthly over a 3 month period using the branched chain DNA assay (bDNA) (Jacobsen et al., 1996), which had a lower limit of detection (LLD) of 50 HIV RNA molecules/ml. All subjects had undetectable plasma virus during this interval.

Figure 1:
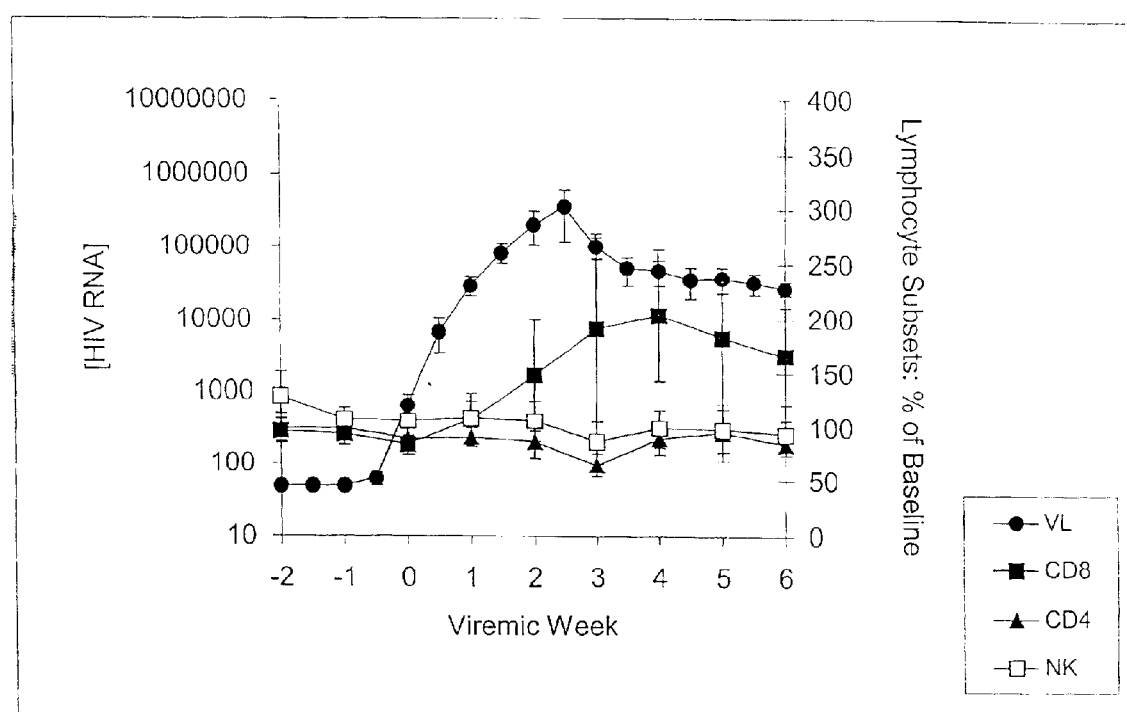
FIG. 1 Changes in plasma HIV RNA concentration after the cessation of Potent anti-retroviral therapy (PART) and changes in the concentrations of circulating lymphocyte subsets after the cessation of PART. Values represent the means and the error bars the SEM of determinations from 9 separate subjects. HIV RNA=filled circle; CD4+ T cells= triangles; CD8+ T cells=filled squares; and NK cells=open squares. Baseline cell concentrations were calculated as the means of 4 separate determinations made monthly, prior to the cessation of PART and are listed in Table 1.

Subsequent to the discontinuation of PART, plasma HIV was monitored twice weekly. Plasma HIV RNA concentrations were determined on EDTA anti-coagulated plasma samples, which were frozen (−70° C.) within 3 hours of phlebotomy. Samples were assayed by Bayer Diagnostics, Emeryville, Calif. Lymphocyte subsets were determined on fresh blood samples by flow cytometry using subset-specific monoclonal antibodies and a FACSCaliber from Becton-Dickinson, San, Jose, Calif. by standard procedures according to the manufacturer. All subjects eventually experienced a relapse of viremia The onset of viremia in each subject was taken as t=day 1. The mean time interval until plasma virus once again became detectable was 19±3 (SEM) days (range 14–39 days). Thereafter, the variation of mean virus concentration in the plasma of all 9 subjects over time is shown in FIG. 1. Once detectable, the plasma virus concentration increased progressively over 2.5 weeks, reaching a mean peak of 375,101±229,139 (SEM) ($\log_{10}$=5.15±0.21) HIV RNA molecules/ml. Thereafter, the virus concentration decreased progressively over the next 4–6 weeks, reaching an apparent trough defined as at least 4 successive measures of HIV RNA that varied less than 3-fold. By 6 weeks from the onset of the viremia, the mean virus concentration had decreased to 31,707±11,851 (SEM) ($\log_{10}$=4.21±0.19) HIV RNA molecules/ml, a drop from the peak viral concentration by an order of magnitude.

The slopes of the initial decline of plasma virus during the first 10 days after the peak plasma HIV concentration for all subjects were calculated and the mean half time (t ½) for decline of plasma HIV for all subjects was 3.5±0.7 (SEM) days (Table 2). However, from the slopes listed in Table 2, there were two distinct rates of viral decline, one with a (t ½)=1.6±0.1 days, and another with a mean (t ½)=5.1±0.7 days (p<0.001, two-tailed T-test). Also, from the data shown in Table 2, the mean magnitude of decline of plasma HIV in the subjects with a rapid rate of viral decline was calculated at 1.37±0.05 $\log_{10}$ HIV RNA molecules/ml vs. a decline of only 0.59±0.15 $\log_{10}$ HIV RNA molecules/ml for those individuals with the slower rate of decline, a difference that was significant (p<0.005, two-tailed T-test).

For 3 months prior to the discontinuation of PART, the concentration of circulating lymphocyte subsets were monitored monthly (see Table 1). Subsequent to the discontinuation of PART, the lymphocytes were monitored weekly. Whole blood (1 ml) was activated in vitro with HIV recombinant p55 antigen (Chiron Corp., Emeryville, Calif., 1 μg/ml) for 6 hours at 37 C. During the last 4 hours, Brefeldin A (Sigma, Inc., St. Louis, Mo., μ/ml) was added to retard cytokine secretion. At the end of the incubation, EDTA (Sigma, 100 mM) was added, the blood was vortexed vigorously for 10 seconds, and the erythrocytes were lysed using 10 ml FACSLysing Reagent. After a 10 minute incubation the leukocytes were separated by centrifugation (500×g, 10 min), then resuspended and frozen (−70 C) in 2 ml R.P.M.I. 1640 tissue cuture medium containing 10% fetal calf serum and 10% dimethyl sulfoxide. Prior to labeling with monoclonal antibodies, the cells were thawed, centrifuged (500×g, 10 min) and permeabilized using FACSPerm. After washing with 3 ml phosphate buffered saline (PBS), the cells were incubated with fluorochrome-conjugated monoclonal antibodies for 30 minutes at room temperature in the dark. The cells were then washed 1× with PBS, and then fixed with 0.5% paraformaldehyde and analyzed by flow cytometry.

Changes in T cells and NK cells over time after discontinuation of PART as a percentage of baseline levels, before discontinuation of PART, are plotted in FIG. 1. The only significant change in the concentration of circulating CD4+ T cells occurred just after the peak of viremia, when there was a 24% decrease compared with baseline levels (p<0.01, paired two tail T-test). Circulating NK cells did not change significantly during the entire interval. By comparison, coincident with the reappearance of viremia, there was a rapid rise in the concentration of CD8+ T cells, such that after 2 weeks of viremia, the CD8+ T cell concentrations had increased >200% of baseline levels. These elevated levels of CD8+ T cells then persisted for the next 3 weeks, as the plasma HIV progressively declined.

TABLE 2

VIRAL DYNAMICS AFTER CESSATION OF PART*

| | Increasing HIV | | | | Decreasing HIV | | | | Max. |
|---|---|---|---|---|---|---|---|---|---|
| | Dbl time | Days to | Peak HIV | | T ½ | Time to | Trough HIV | | Decrease |
| Subject | (days) | Peak | # | (log) | days | Min. (days) | # | (log) | (log) |
| 1 | 1.6 | 18 | 80910 | (4.91) | 1.5 | 10 | 4741 | (3.68) | 1.23 |
| 2 | 2.0 | 14 | 230074 | (5.36) | 1.8 | 17 | 10024 | (4.00) | 1.36 |
| 3 | 1.2 | 10 | 67442 | (4.83) | 1.5 | 18 | 2266 | (3.36) | 1.47 |
| 4 | 2.7 | 28 | 14059 | (4.15) | 7.6 | 9 | 9215 | (3.96) | 0.19 |
| 5 | 1.3 | 14 | 40662 | (4.61) | 5.2 | 28 | 9180 | (3.96) | 0.65 |
| 6 | 1.0 | 14 | 295942 | (5.47) | 5.5 | 24 | 22695 | (4.36) | 1.11 |
| 7 | 2.0 | 21 | 160949 | (5.21) | 3.4 | 7 | 48562 | (4.69) | 0.52 |
| 8 | 1.6 | 16 | 2185670 | (6.34) | 1.6 | 26 | 85782 | (4.93) | 1.41 |
| 9 | 1.6 | 16 | 300203 | (5.48) | 3.9 | 26 | 92901 | (4.97) | 0.51 |
| Mean | 1.6 | 17 | 375101 | (5.15) | 3.5 | 18 | 31707 | (4.21) | 0.94 |
| SEM | 0.2 | 2 | 229139 | (0.21) | 0.7 | 3 | 11851 | (0.19) | 0.16 |

*A two-tailed T-test was used to compare the $\log_{10}$ HIV RNA concentrations from the peak and trough, and those subjects with a rapid t½ (#1, 2, 3, 8) vs. tose with a slow t½ (#4, 5, 6, 7, 9). The doubling times of plasma HIV concentrations and the half times of the declines of HIV RNA concentrations were determined from at least 3 consecutive data points.

To quantify HIV-reactive CD4+ T cells in the subjects prior to the cessation of PART, we monitored intracellular cytokine production by flow cytometry, after a short-term (6 hrs) activation in vitro with the HIV gag polyprotein p55 (Picker, C. J. et al., *Nat Med* 5, 518–25 (1999); Picker, L. J. et al. *Blood* 86, 1408–19 (1995); Waldrop, S. L. et al., *J Clin Invest* 99, 1739–50 (1997). Consistent with the findings of Picker et al. (1999), we found that only one subject (# D3, Table 1) had detectable HIV-specific CD4+ T cells. Thus, there were readily detectable HIV p55-specific CD4+ T cells capable of producing TNF-α (0.29%), IFN-γ (0.31%), and IL-2 (0.16%).

Figure 2:
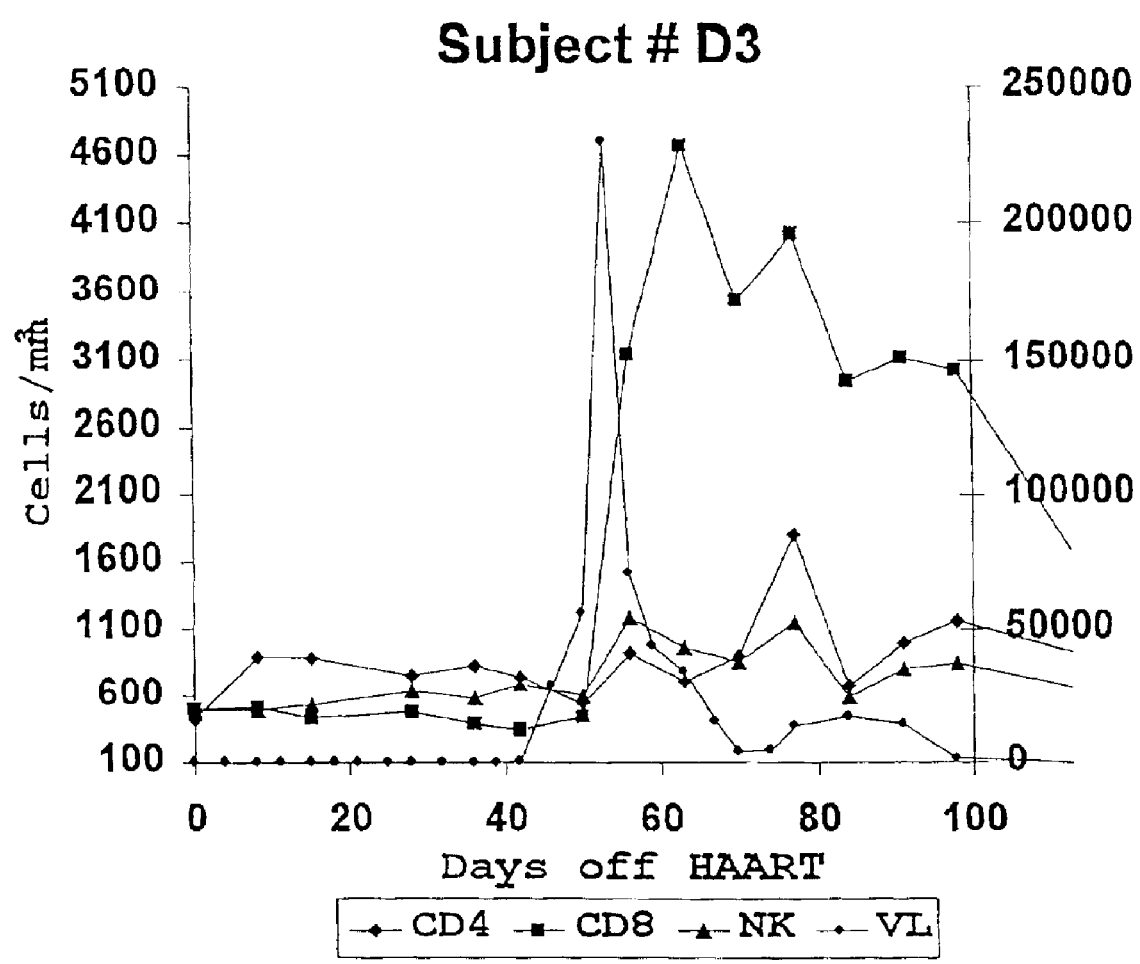
FIG. 2 Changes in plasma HIV RNA concentrations and circulating lymphocyte subset concentrations in subject D3 upon cessation of PART. Symbols: HIV RNA molecules/ml (VL circle), CD4+ T cells (diamond), CD8+ T cells (square), and NK cells (triangle).

The course of this subject after the discontinuation of PART was particularly noteworthy. This individual was known to have a positive HIV serology for 2 years prior to the institution of PART, and received 2 years of PART prior to its discontinuation. Shown in FIG. 2 are the concentrations of circulating lymphocyte subsets plotted together with the plasma HIV RNA after the cessation of PART. Plasma HIV RNA was undetectable for 39 days after the discontinuation of PART, but then rose rapidly to peak at 230,074 HIV RNA molecules/ml at day 53. Subsequently, there was a rapid decrease in circulating virus, so that <1% of the peak viral concentration (1,686 HIV RNA molecules/ml) was still present after 98 days without PART. The changes in circulating lymphocytes were remarkable in relationship to these changes in viral titers. In particular, the CD8+ T cells increased from normal baseline values (577±105 SEM cells/mm3) 8-fold to 4,669 cells/mm3, coincident with the marked drop in plasma HIV RNA. Thereafter, the concentration of circulating CD8+ T cells remained elevated, as the concentration of HIV RNA continued to decline. By comparison, the concentrations of CD4+ T cells and NK cells remained within the normal ranges throughout the study interval.

Given that the rate of viral decline correlated with the magnitude of the decrease in plasma virus concentration, we next examined the changes in CD8+ T cell concentrations as a function of the viral decline. The group with the more rapid rate and magnitude of viral decline mounted a CD8+ T lymphocytosis with a mean peak increase 350% of baseline, while the group with the slower rate and magnitude of viral decline underwent only a mean peak increase of CD8+ T cells 150% of baseline.

Figure 3:
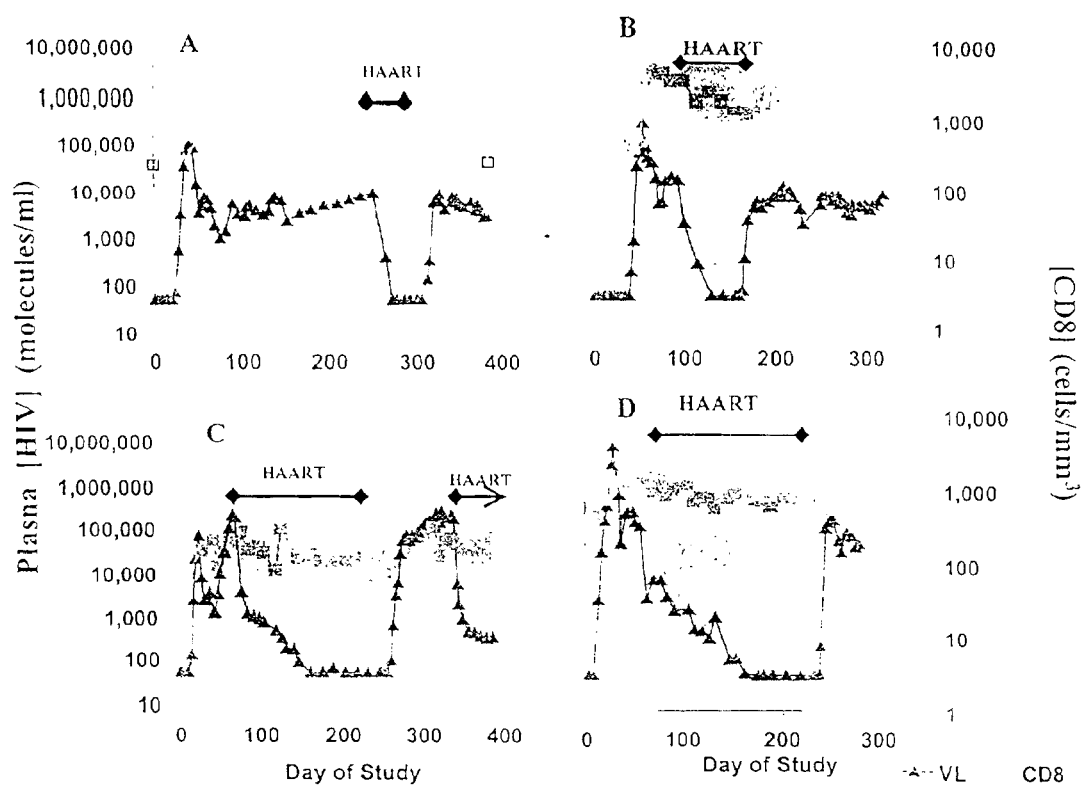
FIG. 3 Viral and CD8+ T cell dynamics after a second interruption of antiviral therapy compared with the first interruption of antiviral therapy. A=subject #1, B=subject #2, C=subject #3, and D=subject #8. HIV RNA—(●), CD8+ cell concentration=(■). Shaded areas represent HAART intervals. Day 0 Study represents the time of the first interruption of HAART. The subjects shown in FIGS. A, B, and D remain off of HAART, whereas, the subject shown in C was placed back on HAART on day 350.

These data suggested that the host immune response might be responsible for the decline in plasma HIV, thereby contributing to the eventual plasma virus concentration at steady state. To test this assumption, 4 of these 9 individuals underwent a second treatment interruption (FIG. 3). The relapse of viremia after the second interruption was similar to the first interruption in terms of the latent period to detectable viremia (14.5±4.1 days) and the rate of doubling (t½=1.5±0.3 days). However, the peak plasma HIV RNA concentration of 3 of these 4 individuals (FIGS. 3A, B, & D) was 1.26±0.14 $\log_{10}$ HIV RNA molecules/ml lower after the second interruption (4.27±0.27 $\log_{10}$ HIV RNA molecules/ml) compared with the first interruption (5.53±0.54 $\log_{10}$ HIV RNA molecules/ml), a difference that was significant (p=0.01, paired T-test). The peak plasma viremia of the fourth subject (FIG. 3C) was identical to the level of viremia after the first treatment interruption. Also shown in FIG. 3 are the CD8+ T cell concentrations, which remained elevated after the first treatment interruption and increased further upon reappearance of viremia after the second treatment interruption. The CD4+ T cell and the NK cell concentrations did not change significantly during the second treatment interruption compared with the first interruption.

Figure 4:
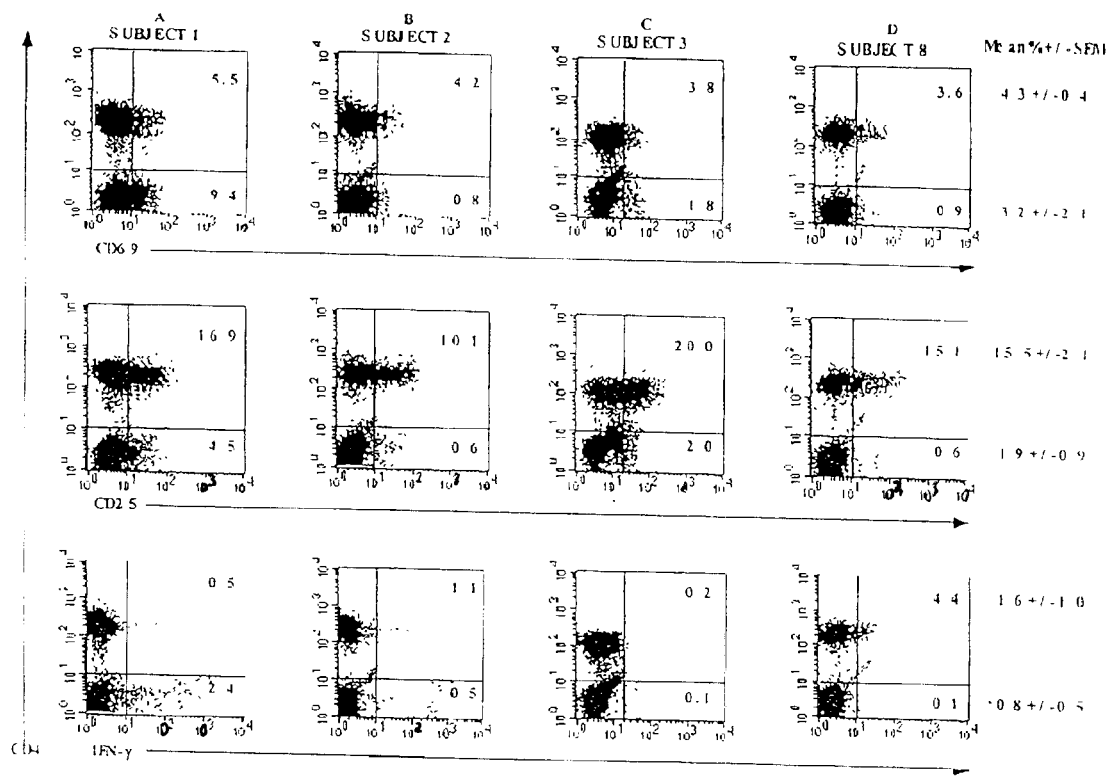
FIG. 4 Expression of activation markers of CD4+ T cells and CD4− T cells after stimulation with HIV p24. Vertical axis=CD4, upper row horizontal axis=CD69, middle row= CD25, lower row=IFN-γ. A=subject #1, B=subject #2, C=subject #3, and D=subject #8. Numbers in right quadrants represent the % of CD4+ (upper) and CD4− (lower) T cells that reacted with the monoclonal antibody directed against the respective activation marker. The numbers in the column on the right represent the mean±SEM of the percentage positive cells from all 4 subjects. The values for control cultures, which received monoclonal antibodies reactive with accessory molecules alone (CD28 & CD49d) without HIV p24, were subtracted from the plots and percentages shown.

To examine the HIV specific reactivity of CD4+ T cells, we performed an 18-hour activation of whole blood with HIV p24 followed by a 4-hour incubation with Brefeldin A to inhibit secretion. Subsequently, the cells were examined by flow cytometry after reaction with fluorochrome-conjugated monoclonal antibodies. Shown in FIG. 4 are the results from experiments performed with blood from the subjects who underwent a second treatment interruption when they had experienced the second CD8+ T lymphocytosis and had reached a stable concentration of plasma virus. Only CD3+ T cells were examined. The results show that a significant percentage of CD4+ T cells from all 4 subjects were stimulated by HIV p24 to express the activation markers CD69 (mean 4.3%±0.45 SEM) and CD25 (mean 15.5%±2.1% SEM). In addition, subjects #1, 2 and 8 also expressed IFN-γ (mean 2.0%±1.2% SEM), while subject #3 had reactivity just above the limits of detection (0.2%). Also depicted in FIG. 4 are the results of the activation markers expressed by CD4– T cells, which are all CD8+, as determined by direct analysis for CD8 expression. There were also CD4– T cells stimulated to express CD69 (mean 3.2%±2.1% SEM) and CD25 (mean 1.9%±0.9% SEM). Moreover, CD4– T cells from subjects #1 and 2 also expressed IFN-γ, whereas the cells from subject 3 and 8 were at the level of detection (0.1%).

It was unexpected to find CD3+, CD4– cells capable of expressing surface markers of activation, and as well, producing detectable intracellular IFN-γ after HIV p24 stimulation. Therefore, to determine whether CD8+ T cells were responding to a short-term activation with p24, the cells were tested directly for reactivity with anti-CD8. The results, shown for subject #1 in FIG. 5 reveal that CD8+ T cells were activated specifically by HIV p24. The analysis was performed as shown in FIG. 5A, by first gating on lymphocytes by size and granularity (R1), then on CD3+ T cells (R3), followed by gates for CD8–(R4), CD8Dim(R5), and CD8+(R6). FIG. 5B depicts the plots for each of these three CD3+ cell populations from the control populations in the top panels, and the HIV p24-stimulated cells in the bottom panels. The cells were tested for reactivity with anti-IFN-γ (vertical) vs. anti-CD56 (horizontal). The bottom left panel CD3+, CD8– T cells (CD4+) shows that a significant fraction of these cells were positive for IFN-γ. However, in addition to these CD8– T cells as shown in the middle and right panels, there were also a significant fraction of CD3+, CD8+ T cells that were positive for intracellular IFN-γ expression. Similar results were obtained when the cells were examined for CD69 and CD25 expression.

Given that NK cells have been found to exert antiviral activity through direct cytolysis as well as by producing antiviral cytokines such as IFN-γ, it was of interest to examine the CD56+ cells for evidence of functional activation, especially when cultured with HIV p24. Accordingly, CD3– cells from subject #1 were also examined for evidence of HIV p24 activation, as shown in FIG.

5C. As many as 33% of CD3−, CD8− cells that express CD56 produced IFN-γ when activated by HIV p55, as do 28% of CD3−, CD8-dim cells that are CD56+. These cells are classic NK cells as defined by the lack of CD3 expression and the expression of CD56, with some cells expressing a low density of CD8. There were no cells that were CD3− but CD8+ (right panels).

Regarding the lymphocyte dynamics following treatment interruption, there was only a slight and transient drop in the concentration of circulating CD4+ T cells that coincided with the peak in viremia. Also, the increase in the concentration of CD8+ T cells was distinctive, given no detectable increase in CD4+ T cells and the lack of any change in the concentration of NK cells. Perhaps even more notable was the timing of the CD8+ lymphocytosis. CD8+ T cells did not increase until well after the return of detectable plasma virus.

The HIV antigen reactivity of CD4+ T cells detected after an in vitro short-term activation was unexpected, in that previous experiments performed by monitoring for antigen-specific lymphocyte proliferation failed to find reactivity in cells from individuals who were infected chronically before therapy (Rosenberg et al., Science, 1997, 278:1447–50). In addition, long-term HAART has been reported to further decrease CD4+ T cell HIV reactivity (Picker et al., Nat Med, 1999, 5:518–25). In this regard, it is important to note that our methods of HIV antigen activation differed from those previously reported (Picker et al., 1999). We found that an overnight (18 hrs) incubation yielded more information than a shorter, 6 hour incubation as to the frequency of antigen reactive cells, because it was possible to assay for the expression of both CD69 and CD25 as surface markers of activation as well as for intracellular IFN-γ expression. The expression of CD25 is optimal after this time interval, whereas it is not yet increased after only a 6-hour incubation. The frequency of CD4+, HIV p24-reactive CD25+ T cells after the second treatment interruption averaged 15.5%, or 1:6 CD4+ T cells, which is an exceptional frequency for a single antigenic protein.

These methods uncovered HIV-specific reactivity by CD8+ T cells as well as NK cells. These responses were HIV specific in that they were only observed in cultures to which HIV p24 had been added, and were not present in 3 of 4 subjects when CMV antigen was tested as a control.

Our data indicate that chronically infected subjects are able to mount an effective immune response to HIV. Accordingly, upon the reappearance of viremia host defenses react to limit virus production, thereby leading to a decrease in plasma virus concentration. Moreover, our results dispel any fear that daily, low-dose IL-2 therapy is dangerous, either before or after the withdrawal of anti-virals. Our results also show that viral replication is not stimulated by low-dose IL-2 when PART is administered. Moreover, viral replication is actually suppressed by the immune system when IL-2 is administered daily in low doses after the cessation of the anti-virals.

Example 3

Clinical Trial of IL-2 Immunotherapy in HCV

To design the most direct and simplest protocol to test the efficacy of the addition of IL-2 to standard therapy, we considered both the toxicity profiles of IL-2 and IFN-α which are quite similar, as well as the proposed mechanisms of action of each cytokine. Both IL-2 and IFN-α cause non-specific constitutional symptoms, such as fever, myalgia, and malaise. However, these symptoms are dose-dependent, and can be ameliorated by dose reductions. Even so, the simultaneous initiation of both of these cytokines would preclude the identification of which cytokine might be responsible for any constitutional symptoms encountered. Therefore, we felt it best to stagger the initiation of one cytokine in relationship with the other.

IFN-α causes a rapid diminution in plasma virus, which can be several orders of magnitude. Since IL-2 responsiveness, especially in antigen-specific T cells and B cells, depends upon continuous antigen stimulation, it was considered unwise to institute a marked reduction in viral antigen load with IFN-α prior to the initiation of IL-2 immunotherapy, In contrast, as IL-2 monotherapy has been found to be safe in HCV patients, it was considered best to initiate IL-2 immunotherapy prior to the institution of IFN-α therapy.

The timing of the institution of IFN-α after IL-2 was the next consideration. From our experience with IL-2 in HIV patients, we are able to detect an increase in NK cells and CD4+ T cells by 1 month, which progresses throughout the first 6 months of therapy. Three months of IL-2 therapy before the institution of IFN-α was chosen, so as to allow this time interval for IL-2 to promote the expansion of antigen-activated lymphocytes.

Experimental Protocol

The study compares two regimens:

Group I: Standard therapy: IFN-α (3 million U TIW)+ Ribavirin (1000–1200 mg/d) for 48 weeks Group II: IL-2 (1.2 million CU/m$^2$/d) for 12 weeks, then IL-2+ Standard therapy for an additional 48 weeks. The Schematic treatment plan and laboratory evaluation schedule is as follows:

| | Group I (IFN-α + ribavirin) | | | | | | | | | | | | | |
|---|---|---|---|---|---|---|---|---|---|---|---|---|---|---|
| Time on IFN/Ribavirin (weeks) | 0 | 1 | 2 | 4 | 8 | 12 | 16 | 20 | 24 | 28 | 32 | 36 | 48 | 72** |
| CBC diff plts | X | X | X | X | X | X | X | X | X | X | X | X | X | X |
| biochem | X | | | X | | X | | | X | | | X | X | X |
| ALT | X | | X | X | X | X | X | X | X | X | X | X | X | X |
| ggtp | X | | X | X | X | | | | X | | | X | X | X |
| tsh | X | | | | X | | X | | X | | | X | X | |

-continued

| | | | | | | | |
|---|---|---|---|---|---|---|---|
| hcv by PCR | X | | X* | X | X | X | X |
| b & t cells | X | | | X | X | X | X |
| CPLp assay | X | | | X | X | X | X |

| | Group II (IFN-α + ribavirin + IL-2) | | | | | | | | | | | | | | | | | | |
|---|---|---|---|---|---|---|---|---|---|---|---|---|---|---|---|---|---|---|---|
| time on IFN/Ribavirin (weeks) | | | | | | | 1 | 2 | 4 | 8 | 12 | 16 | 20 | 24 | 28 | 32 | 36 | 48 | 72** |
| time on IL-2 (weeks) | 0 | 1 | 2 | 4 | 8 | 12 | 13 | 14 | 16 | 20 | 24 | 28 | 32 | 36 | 40 | 44 | 48 | 60 | 84** |
| CBC diff plts | X | | X | X | X | X | X | X | X | X | X | X | X | X | X | X | X | X | X |
| biochem | X | | X | | X | | | X | | X | | X | | X | | | X | X | X |
| ALT | X | | X | X | X | | | X | X | X | X | X | X | X | X | | X | X | X |
| ggtp | X | | X | X | X | | | X | X | X | | | X | | | | X | X | X |
| tsh | X | | | X | | X | | | X | X | X | | X | | X | | X | X | |
| hcv by PCR | X | | | X* | | X | | | X | | X | | X | | | | | X | X |
| b & t cells | X | | | | | X | | | | X | | X | | X | | | X | X | X |
| CPLp assay | X | | | | | X | | | | X | | X | | X | | | X | X | X |

1. Height, weight, and physical examination: at baseline and when clinically indicated
2. Laboratory evaluation schedule is listed in the table above
3. Labs to be sent to New York Hospital Laboratory: CBC, differential, platelets, biochemistry panel, ggtp, tsh, and lymphocyte subset analysis.
4. HCV quantitation will be performed by Specialty Labs (Santa Monica CA). An RT-PCR assay will be performed. The lower limit of detection of the assay is 200 copies of HCV per ml of plasma.
5. Intracellular flow cytometry: Three color flow cytometry will be performed. Two colors will be used to identify the outside of the cell (including CD3, CD4 and CD8) and one color will be used to identify the expression of intracellular cytokines (including IL-2, IFN-γ, TNF-α, and IL-4).
*HCV titer will be measured on ⅓ of the subjects in each group at time points indicated to evaluate the kinetics of HCV disappearance in both groups.
**24 weeks after the completion of therapy.

Sixty-two subjects are randomly assigned to either group. Following 48 weeks of therapy with IFN-α/Ribavirin, all therapy is discontinued and each group is evaluated for sustained viral response 6 months later. The primary endpoint is determination of detectable plasma virus after 24, 48 and 72 weeks of standard therapy. A sustained viral response is defined as the absence of detectable virus assayed by the standard PCR method. Liver function tests are also monitored, but are not included in the definition of a sustained viral response.

The secondary endpoint is the determination of the immune reactivity, both in general and in particular to HCV. Immunological assessment is performed at the same time intervals as the assays for plasma virus, i.e. at 24, 48 and 72 weeks of standard therapy.

As diagramed in the treatment schema, individuals who randomize to receive standard therapy are evaluated after 24 weeks of treatment for the persistence of plasma virus. If plasma virus is present at 24 weeks, these individuals are considered treatment failures and discontinue the protocol. Individuals assigned to Group II are also evaluated after 6 months of standard therapy, as shown in the diagram. If plasma virus is still detectable at this time interval, the subjects are considered non-responders and stop all therapy. In both instances, all subjects who discontinue therapy are considered non-responders.

A final measurement of viral load and liver function is performed 24 weeks following cessation of therapy. Individuals with an undetectable plasma virus are considered to have had a sustained viral response.

Patient Selection

Thirty-one (31) subjects are enrolled in each arm of the principal study for a total of 62 subjects. Eligibility and exclusion criteria are listed below.

Conditions of Eligibility
1. Hepatitis C antibody positive
2. HCV RNA+ by PCR assay
3. ALT>50 but <200 U/L
4. Greater than Grade 1, stage I disease activity on liver biopsy
5. Prothrombin time £ 2× INR
6. Platelets >75,000
7. Creatinine (serum)<2.0
8. Neutrophils >1000/mm$^3$
9. Hgb >10/dl
10. Written, informed consent must be obtained in all cases
11. Negative urine pregnancy test in women of childbearing age
12. All races and both sexes will be included
13. Age >18 years Conditions for Exclusion
1. Previous IFN-α therapy
2. Any liver disease other than hepatitis C disease
3. Uncompensated cirrhosis
4. Grade 1, stage I disease activity on liver biopsy
5. Uncontrolled infection, except hepatitis C
6. HIV co-infection
7. Any cardiac condition that cannot be controlled by medication
8. Any CNS or psychiatric illness uncontrolled by medication
9. Concurrent therapy with corticosteroids or immune modulating agents
10. Pregnant or nursing women (all women of child bearing age should be using effective contraception)

11. Any history of malignancy

12. Any history of asthma

Drug Formulation, Procurement and Administration a) IFN-α: Interferon α-2b (IFN-α recombinant for injection) is obtained from Schering (Kenilworth, N.J.). After reconstitution, the 3 million IU vial contains 3 million IU of interferon α-2b, recombinant, 20 mg glycine, 2.3 mg sodium phosphate dibasic, 0.55 mg sodium phosphate monobasic, and 1.0 mg human albumin. Based on the specific activity of approximately $2 \times 10^8$ IU/mg protein, the quantity of interferon α-2b in the vial is 0.015 mg. A powder for injection is reconstituted with the provided Diluent for INTRON A Interferon α-2b, recombinant for injection (bacteriostatic water for injection) containing 0.9% benzyl alcohol as a preservative.

b) Ribavirin: Ribavirin is obtained from Schering (Kenilworth, N.J.). Ribavirin capsules consist of a white powder in a white opaque gelatin capsule. Each capsule contains 200 mg ribavirin and the inactive ingredients microcrystalline cellulose, lactose monohydrate, croscarmellose sodium and magnesium stearate. The capsule shell consists of gelatin, sodium lauryl sulfate, silicon dioxide, and titanium dioxide.

c) IL-2: IL-2 (PROLEUKIN®) is obtained from Chiron (Emeryville Calif.). Proleukin is supplied as a sterile lyophilized cake. When reconstituted with 1.2 ml sterile water for injection, each ml contains 1.1 mg PROLEUKIN®, 50 mg mannitol, and 0.18 mg sodium dodecyl sulfate, buffered with approximately 0.17 mg monobasic and 0.89 mg dibasic sodium phosphate to a pH of 7.5 (range 7.2 to 7.8).

Dosage Adjustments a) IL-2: The initial dose of IL-2 used in this study is based on our studies in HIV infection. Individuals with HIV were able to tolerate rIL-2 at $1.2 \times 10^6$ IU/m²/day. At this dose, plasma concentrations were attainable that saturated 70% of high affinity IL-2 receptors (25 pM). Peak plasma levels are measured at two hours after initial IL-2 injection. Dosage adjustments of IL-2 are made under the following circumstances:

(1) IL-2 Dosage reduction: If a subject experiences WHO grade I systemic toxicity, and is unable to tolerate the daily dose of rIL-2 at $1.2 \times 10^6$ IU/m²/day, the dose is reduced to $0.9 \times 10^6$ IU/m²/day. In the event that toxicity continues, the dose is decreased to 0.75 IU/m²/day, which is halfway between the previous dose and the dose we have previously determined to be ineffective (0.6 IU/m²/d).

(2) IL-2 Dosage increase: In the event that peak plasma levels of IL-2 are not sufficient to saturate 50% of the high affinity IL-2 receptors, and the subject is not experiencing dose limiting toxicity, the dose of IL-2 may be increased to $1.8 \times 10^6$ IU /m²/day. This dose is midway between the starting dose and the dose found to be toxic in 100% of patients ($2.4 \times 10^6$ IU /m²/d). In the event that toxicity occurs, the dose is adjusted to $1.4 \times 10^6$ IU 1m²/day, and if there is still toxicity, the dose will be returned to $1.2 \times 10^6$ IU /m²/day.

In the event that peak plasma IL-2 concentrations in the therapeutic range of 10–25 pM are not attained, and there is no systemic toxicity, the dose is increased in 50% increments until either side effects or a therapeutic range is achieved.

b) IFN-α and Ribavirin: For events WHO grade II, other than anemia, the dose of ribavirin is reduced to 1.5 MIU TIW, and the dose of ribavirin is reduced to 600 mg/day. If the effects persist, the drugs are discontinued. The dose of ribavirin is decreased to 600 mg/day for a hemoglobin below 10 g/dl, and are discontinued if the hemoglobin falls below 8.5 g/dl Expected Toxicity a) IL-2: Based upon the results of our prior studies with subcutaneous administration of IL-2, no systemic toxicities are expected. Local inflammation at the site of injection will occur and consist of mild erythema and induration. There should be no pain, but mild pruritus can occur. The reaction is maximal at 24 hours after injection, and is cleared by 72 hours after injection. As the sites of injection will be rotated between the trunk and lower extremities, local inflammation is not expected to limit therapy. At the doses of IL-2 to be used in this study, liver toxicity has not been described.

b) IFN-α/Ribavirin: The adverse experiences attributable to combination IFN-α/ribavirin therapy are listed in the table 1 below. Most of these are mild to moderate in severity, some were transient and most diminished over time.(PDR-Schering).

TABLE 2

Adverse effects of IFN-α/Ribavirin therapy

| Adverse Experience | % of Patients |
|---|---|
| fever | 32 |
| headache | 66 |
| myalgia | 61 |
| rigors | 43 |
| nausea | 47 |
| fatigue | 60 |
| arthralgia | 29 |
| anorexia | 21 |
| Hemoglobin 9.5–10.9 g/dl | 21 |
| Hemoglobin 8.0–9.4 g/dl | 4 |
| WBC 2.0–2.9 k/ml | 45 | c) Hypersensitivity Reactions

IL-2                                                                                          (1)

No systemic allergic reaction has been documented in the literature thus far. However, if a patient has a definite systemic allergic reaction, that individual will be withdrawn from IL-2 therapy.

IFN-a/Ribavirin                                                                               (2)

Hypersensitivity reactions to IFN-a/Ribavirin have not been described (PDR).

F. Other Medications Allowed

All medications will be allowed with the exception of drugs listed in section G below, "medications not allowed"

G. Medications Not Allowed

1. Systemic steroids

2. Inhaled steroids

3. Inhaled bronchodilators

4. Any substance with known immunomodulatory actions

H. Toxicity Criteria

A graded toxicity (WHO) scale will be used. Laboratory toxicities are defined by two consecutive determinations.

For grade I toxicity, treatment with the causative agent(s) will be delayed until there is a return to baseline or grade 0 toxicity. The patient will then receive a decreased dose of the responsible agent as outlined above in section VI C, "Dosage adjustment"

I. Criteria for Subject Removal from the Study

Patients may withdraw or be removed from the study in the following instances:

1. Intercurrent illness which would, in the judgment of the investigators, affect assessment of clinical status to a significant degree
2. Unacceptable toxicity (WHO>1) after appropriate dosage adjustments have been made
3. Disease progression: patients whose ALT increases by >3 fold on two separate occasions, or whose HCV titer increases by >5 fold on two separate occasions
4. Patient noncompliance, or request to withdraw
5. Pregnancy J. Statistical Analysis The primary objective of the statistical analysis is to compare the 6 month viral response rates between patients randomized to IFN+ribavirin and those randomized to IFN, ribavirin & IL-2.

Our hypothesis is that after 6 months of combined therapy with IL-2, IFN and ribavirin, we will be able to induce a response rate 30% better than IFN and ribavirin. The known response rate after 24 weeks of treatment with IFN and ribavirin is 53%. In our work, we feel that an 83% virologic response rate after 24 weeks of IFN, ribavirin and IL-2 represents a clinically important improvement. Based on that, we have performed the following sample size calculation. In order to achieve 80% power to detect an increase in the response rate to 83% in the IL-2 arm, a sample size of 31 patients per arm will be required (two-tailed test, alpha= 5%).

Viral and biochemical measurements will also be made and reported at 12, 24 and 72 weeks, however the sample size has not been calculated for these measurements. Posthoc analyses will be done as indicated with these data.

K. Immunological Evaluations

We anticipate that the CD8+ T cells may well have a higher frequency of IFN-γ and TNF-α CPLp. Accordingly, determination of the polyclonal CPLp frequencies and absolute numbers of CPLp for each cytokine serve as useful indicators of overall immune responsiveness during the two arms of the treatment protocol. Determinations of polyclonal CPLp frequencies are performed at time 0, and at 12, 24, 48 and 72 weeks while the individuals are on study. These studies are the first to evaluate CPLp in real time while patients are on an experimental treatment protocol. It is anticipated that the evaluation of polyclonal CPLp frequencies and absolute numbers will correlate with disease status, and also will change with therapeutic intervention. Therefore, these experiments are an attempt, for the first time, to evaluate the functional capacity of T cells in a clinical study using this assay.

Ultimately, one goal of our studies will be to identify the functional status of antigen-specific cells. This assay is designed to identify primarily CD4+ T cells that produce cytokines in response to specific antigen stimulation. The assay is performed with 1 ml of whole blood. The antigen-activation step is performed in the presence of co-stimulation with MoAbs reactive with CD28 and CD49 for 2 hours without the secretion inhibitor, Brefeldin A, which is then added for an additional 4 hours, prior to lysing the RBCs and permeabilizing the leukocytes. Subsequently, the cells are stained simultaneously with directly fluorochrome-conjugated MoAbs reactive with surface markers and cytokine (Waldrop, et al, *J. Clin. Invest.* 99(7) 1739–50, 1997). Chiron has agreed to supply HCV antigens for these assays.

The flow cytometry assay is supplemented with simultaneous in situ hybridization to detect the frequency of cells that are positive for cytokine mRNA, and also with simultaneous immunohistochemistry. These approaches will be important, not only to validate the CPLp flow cytometry assays, but they will be especially important if we find that the frequency of antigen-reactive cells is very low, below the limits of detection by the flow cytometer, i.e. <0.1% of activated cells. In this regard, it is important to mention that cells are stained with CD69, which allows one to gate on only cells that express this activation marker, which improves the sensitivity of detection of infrequent reactive cells.

These determinations are supplemented by enumeration of surface markers by flow cytometry, and include the determination of lymphocyte subsets (CD4, 8, 20 and 56). T cell maturation state, i.e. naive vs. memory, is monitored by CD45 RA vs. RO, combined with CD62L. The state of activation of T cells is monitored using reactivity to CD25 and CD69 MoAbs.

These immunologic assays have been chosen, in large part, because they can be accomplished with very small volumes of blood, only ~5 ml. By comparison, standard proliferation assays and chromium release cytotoxicity assays require separation of the mononuclear cells, and consequently larger amounts of blood (often 500–1000 cc), as well as much more laboratory preparation time.

We will utilize a real-time assay to help us follow the immunologic function on an individual cell basis. We have adopted the technique of a short-term (4–6 hours) polyclonal activation in the presence of an inhibitor of secretion, such as Brefeldin A or monensin, originally developed by Openshaw et al. *J. Exp. Med.* 182(5): 1357–67, 1995. This method permits the accumulation of cytokines within the Golgi apparatus, so that it is possible to detect intracellular cytokines using fluorochrome-labeled monoclonal antibodies and the flow cytometer. Because the cells are activated in vitro, rather than assayed directly without stimulation, we are actually assaying the capacity of the cells to express their cytokines genes within a few hours. In effect, these cells are the Cytokine Producing Lymphocyte Precursors (CPLp) which are analogous to the CTLp that are assayed for their capacity to lyse target cells after an in vitro activation step.

To establish the assay in our laboratory, and to determine the ranges and mean values for CPLp, peripheral blood cells from 15 normal individuals were monitored after a 4-hour polyclonal activation with phorbol myristic acetate and calcium ionophore.

The results are remarkable in that the percent CPLp for each cytokine tested is very consistent. Thus, 60% of CD4+ T cells produced IL-2 detectable by this method, compared with 30% CD8+ T cells. Below in table C-3 is a summary of the values for other cytokines tested in this manner.

TABLE C-3

CPLp from CD4+ and CD8+ T cell subsets

| Cytokine | % Cytokine-positive cells | |
|---|---|---|
| | CD4 | CD8 |
| IL-2 | 62 ± 4 | 30 ± 5 |
| IL-4 | 3 ± 0.3 | 2 ± 0.1 |
| IFN-γ | 23 ± 2 | 44 ± 4 |
| TNF-α | 77 ± 2 | 46 ± 6 |

It is noteworthy that there is a narrow range of normal numbers of CPLp, and that the percentages are not identical, indicating that there is no a coordinate activation of all cytokines genes. Instead, these data are consistent with independent regulation of the cytokines genes with a single cell.

The results are significantly different from normal in HIV+ individuals, as summarized in Table C-4.

TABLE C-4

CPLp from CD4+ and CD8+ cell subsets of normals (n = 15) and HIV+ Individuals (n = 52)

| T cells | Cytokine | % Cytokine-positive Cells | | |
|---|---|---|---|---|
| | | Normals | HIV | p* |
| CD4+ | IL-2 | 62 ± 4 | 51 + 2 | <0.0005 |
| | IL-4 | 3 ± 0.3 | 5 ± 1 | NS |
| | IFN-γ | 23 ± 2 | 22 ± 5 | NS |
| | TNF-α | 77 ± 2 | 72 ± 2 | NS |
| CD8+ | IL-2 | 30 ± 5 | 18 ± 1 | <0.0005 |
| | IL-4 | 2 ± 0.1 | 2 ± 0 | NS |
| | IFN-γ | 44 ± 4 | 73 ± 2 | <0.0001 |
| | TNF-α | 46 ± 6 | 65 + 2 | <0.0001 |

*Data from HIV+ Individuals were compared with data normals using the Student's T Test.

Thus, by comparison to normals, there is a deficiency of IL-2 CPLp in both the CD4+ and the CD8+ T cell subset. When there are also fewer circulating CD4+ T cells, it is readily apparent that there is a deficiency of the absolute concentration of cells capable of producing IL-2 when activated polyclonally. In contrast to these findings with IL-2 CPLp, there are normal percentages of IL4, IFN-γ and TNF-α CLPp in the CD4+ T cell subset, so that the defect is specific for IL-2 CPLp. Among other things, this provides a rationale for IL-2 therapy in this infection.

Examination of the frequency of CD8+ CLP1 in HIV+ subjects revealed a marked increase in both IFN-γ and TNF-α CPLp. Given that there is also usually an increase in the concentration of circulating CD8+ T cells, it is easily appreciated that there is a more than doubling IFN-γ and TNF-α CPLp in HIV infection. Accordingly, our results do not support the hypothesis that there is a switch to TH2 type cytokine production as a consequence of HIV infection.

We are also developing antigen-specific CPLp assays, which will be of obvious benefit in monitoring the effect of IL-2 immunostimulatory therapy. In collaboration with Vernon Maino and Cory Waters at Becton-Dickinson, we are just now beginning to assay HIV antigen-specific CPLp. They have tested several different source of antigen, and have identified p55 as an antigen, which encodes the core polyprotein, that yields detectable CPLp in 100% HIV+ long term non progressors. Interestingly, no patients with long term viral suppression (>48 weeks) from antiretroviral therapy had measurable CPLp responses (Pitcher et al., 6th Conference on Retroviruses and Opportunistic Infections Abstracts, Abstract #27 1999:72).

M. Experimental Laboratory Methods

1. Polyclonal and Antigen-Specific CPLp Assays

Whole blood is aliquoted into 5-ml polypropylene tubes (1 ml/tube). Stimuli are added at appropriate concentrations (PMA, 25 ng/ml; Ionomycin, 1 ug/ml) together with Brefeldin A (10 ug/ml). The blood is incubated for 4 hours at 37 C. For staining with fluorochrome-labeled antibodies, 100 ul of the stimulated blood are lysed with 900 ul of FACSLysing solution (10 minutes @ Room Temperature (RT)), then the cells are permeabilized with 0.5 ml of FACSPermeabilizing solution (10 minutes @ RT). The cells are then washed with 2 ml PBS, 0.5% BSA, 0.1% NaN3. Fluorochrome-labeled MoAbs (20 ul) are then added for 30 minutes, the cells are then washed and fixed with 1% paraformaldehyde and stored @ 4 C prior to analysis by flow cytometry.

The procedure is essentially identical when assaying for antigen-specific activation, except that the whole blood is activated with specific antigen in the presence of the co-stimulators anti-CD28 and anti-CD49 for 2 hours prior to the addition of Brefeldin A, to allow for antigen processing and presentation to occur in the absence of the secretion inhibitor. Also, the cells are stained with-MoAb reactive with CD69, in addition to subset surface molecules, to select for activated cells during the analysis phase.

2. InSitu Hibridization Assays

The probes used are anti-sense, single-stranded RNA molecules produced by transcription from a T3 or a T7 primer of a cytokine cDNA insert cloned into either pBluescript or pGEM. For digoxigenin-labeled probes, 1.0 μg of linearized cDNA template is incubated with 50 U of RNA polymerase in transcription reaction mix at 37 C for 2 hrs. The DNA template is then removed with RNase-free DNase. Recovered cells are cytocentrifuged onto RNase-free glass slides, air dried then fixed in 3% paraformaldehyde, and washed with 2xSSC. The slides are pre-hybridized with 4xSSC, then probed overnight at 50 C in humid chambers. Following washes, the slides are developed by incubation for 1 hr at RT with anti-digoxigenin-alkaline phophatase conjugated MoAb. After washing substrate solution is applied ON at 4 C. The color reaction is stopped and the cells observed with bright-field microscopy (Bucy et al., *J Exp Med.* 180(4):1251–62 1994).

3. Immunohistochemical Staining

For detection of cytokine producing cells, the same methods of antigen activation and inhibition of cytokine secretion with Brefeldin A will be used as described for the CPLp assay by flow cytometry. Subsequently, cytospin preparations will be incubated at RT with the same cytokine-reactive MoAbs used for the flow cytometry assays. Bound antibody is detected with biotinylated anti-mouse Ab, then developed with horseradish peroxidase-conjugated avidin. Cells can be counterstained with methyl green or hematoxylin and observed and counted with brightfield microscopy.

What is claimed is:

1. A method for enhancing the ability of the immune system to mount an effective immune response after the discontinuation of antiviral drug therapy for Human Immunodeficiency Virus, comprising administering to a subject a composition comprising IL-2 in an amount effective to maintain at least a normal concentration of circulating CD4+ T cells and an elevated concentration of CD8+ T cells and Natural Killer cells without eliciting toxicity of Grade 1 or higher as defined by the World Health Organization.

2. The method of claim 1, wherein the subject has undetectable plasma viral RNA levels upon discontinuation of antiviral drug therapy.

3. The method of claim 1, wherein the subject has discontinued HAART.

4. The method of claim 1, wherein the subject has discontinued PART.

5. The method of claim 1, wherein the amount of IL-2 administered is about 100,000 to about 500,000 $IU/m^2$ body surface/day.

6. The method of claim 1, wherein the amount of IL-2 administered is about 15,000 to about 1,500,000 $IU/m^2$ body surface/day.

7. The method of claim 1, wherein the subject is administered IL-2 prior to vaccination.

8. The method of claim 1, wherein the IL-2 composition further comprises a pharmaceutical carrier.

* * * * *

UNITED STATES PATENT AND TRADEMARK OFFICE
CERTIFICATE OF CORRECTION

| | | |
|---|---|---|
| PATENT NO. | : 6,921,530 B1 | |
| APPLICATION NO. | : 09/708635 | |
| DATED | : July 26, 2005 | |
| INVENTOR(S) | : Kendall A. Smith | |

It is certified that error appears in the above-identified patent and that said Letters Patent is hereby corrected as shown below:

Column 1 line 6-8, please delete the first paragraph and replace it with the following:

This invention was made with government support under R01AI041381 from the National Institute of Allergy and Infectious Diseases ("NIAID"). The government has certain rights in the invention.

Signed and Sealed this

Eleventh Day of November, 2008

JON W. DUDAS
*Director of the United States Patent and Trademark Office*